United States Patent
Takahashi et al.

(10) Patent No.: US 7,746,981 B2
(45) Date of Patent: Jun. 29, 2010

(54) RADIATION IMAGE DETECTOR AND PHASE CONTRAST RADIATION IMAGING APPARATUS

(75) Inventors: Kenji Takahashi, Ashigarakami-gun (JP); Yoshihiro Okada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 53 days.

(21) Appl. No.: 12/263,006

(22) Filed: Oct. 31, 2008

(65) Prior Publication Data
US 2009/0110144 A1   Apr. 30, 2009

(30) Foreign Application Priority Data

| Oct. 31, 2007 | (JP) | ............................. 2007-284427 |
| Oct. 31, 2007 | (JP) | ............................. 2007-284564 |
| Sep. 11, 2008 | (JP) | ............................. 2008-232866 |

(51) Int. Cl.
*H05G 1/64* (2006.01)
(52) U.S. Cl. .................. 378/98.8; 250/370.11
(58) Field of Classification Search .................. 378/36, 378/62, 98.8; 250/370.08, 370.09, 370.11
See application file for complete search history.

(56) References Cited

U.S. PATENT DOCUMENTS

| 5,812,629 A | 9/1998 | Clauser ....................... 378/62 |
| 7,180,979 B2 | 2/2007 | Momose ....................... 378/62 |

FOREIGN PATENT DOCUMENTS

| JP | 2006-259264 A | 9/2006 |
| JP | 2007-203063 A | 8/2007 |

OTHER PUBLICATIONS

Franz Pfeiffer, et al., "Phase retrieval and differential phase-contrast imaging with low-brilliance X-ray sources", Nature Physics Letters, Mar. 2006, pp. 258-261, vol. 2, No. 1.
L. M. Chen, et al., "Phase-contrast x-ray imaging with intense Ar Kα radiation from femtosecond-laser-driven gas target", Applied Physics Letters, May 2007, vol. 90, No. 211501 (pp. 211501-211503).

*Primary Examiner*—Courtney Thomas
(74) *Attorney, Agent, or Firm*—Sughrue Mion, PLLC

(57) ABSTRACT

A phase contrast radiation imaging apparatus is includes a radiation source, a diffraction grating, and a radiation image detector. The radiation image detector is equipped with a charge generating layer that generates electric charges when irradiated with radiation, and charge collecting electrodes that collect the electric charges. The charge collecting electrodes are linear electrode groups, constituted by linear electrodes which are arranged at a constant period and are electrically connected to each other, provided to have different phases from each other. Thereby, use of a conventional amplitude diffraction grating is obviated.

12 Claims, 18 Drawing Sheets

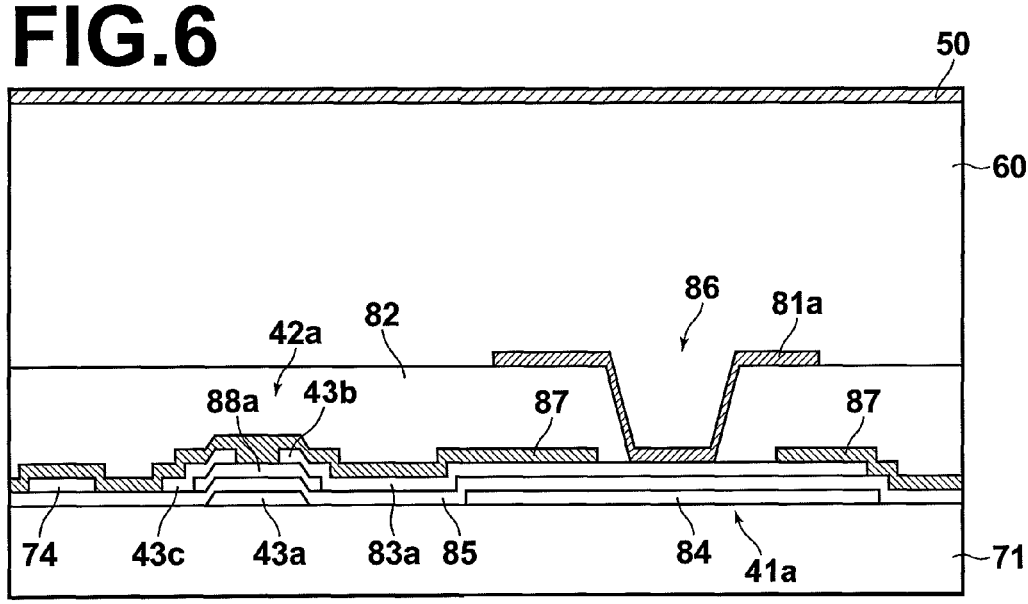
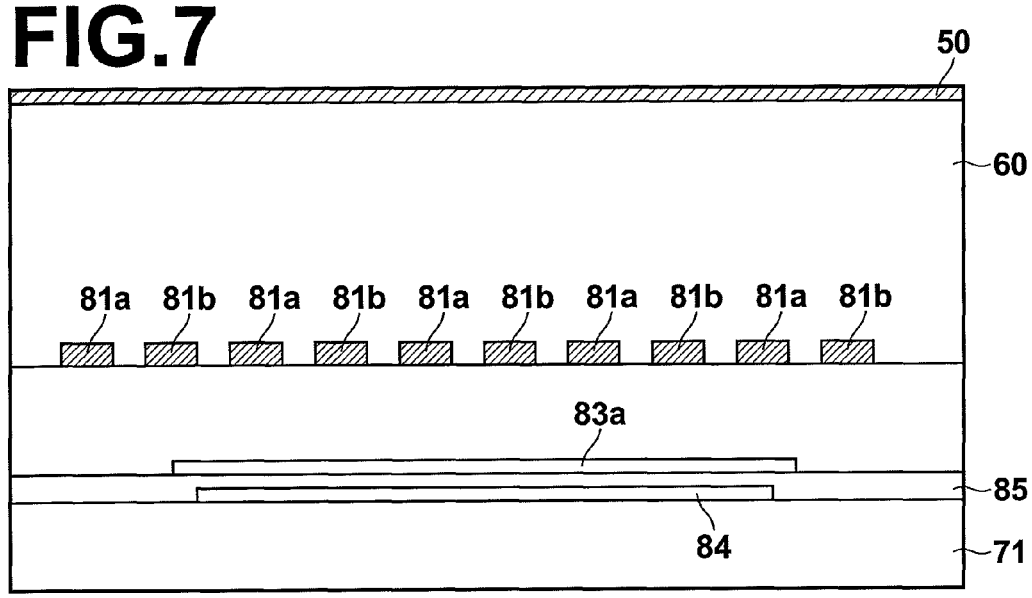

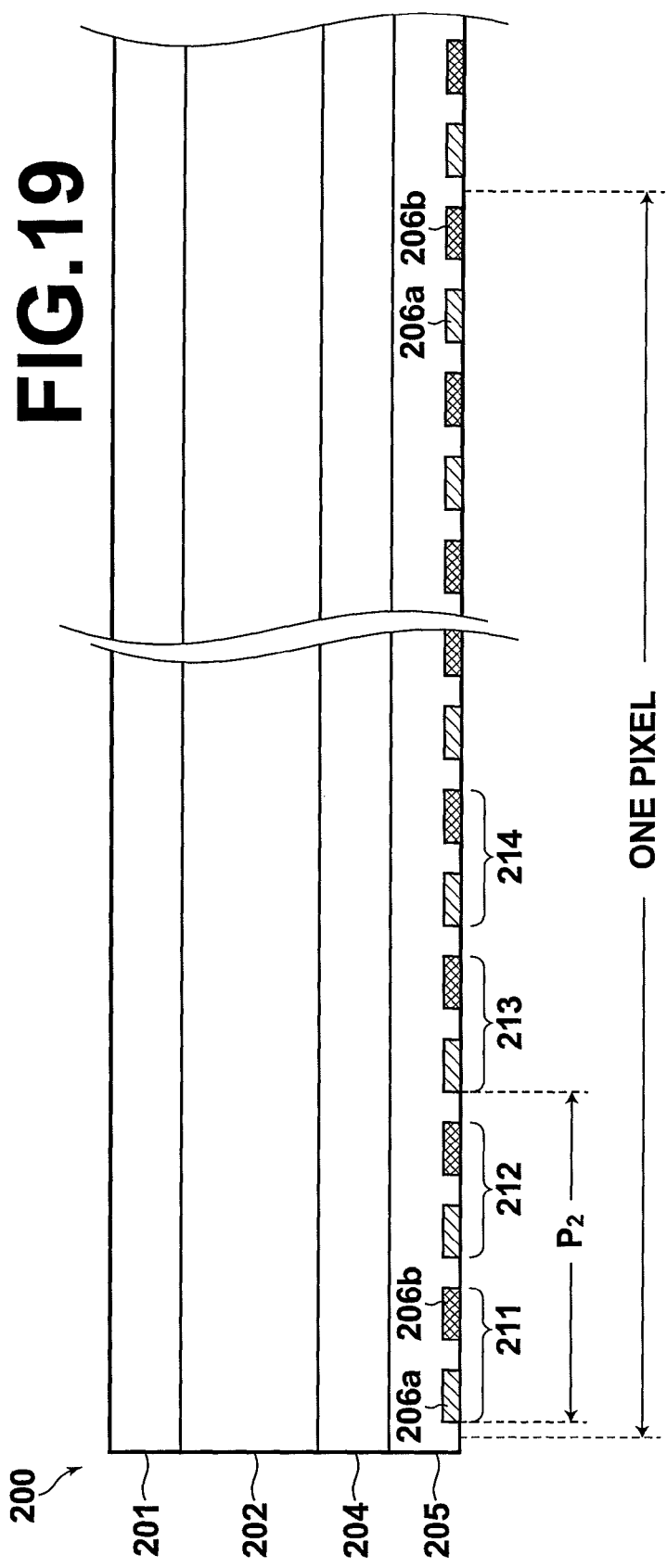

RADIATION IMAGE DETECTOR AND PHASE CONTRAST RADIATION IMAGING APPARATUS

BACKGROUND OF THE INVENTION

1. Field of the Invention

The present invention relates to a phase contrast radiation imaging apparatus and a phase contrast radiation imaging method that utilize a Talbot interferometer, and a radiation image detector which is employed by the phase contrast radiation imaging apparatus.

2. Description of the Related Art

The application of Talbot interferometers, in which the Talbot effect is generated by a diffraction grating and another diffraction grating is used to generate Moire fringes, to the field of X ray imaging is being investigated (refer to U.S. Pat. Nos. 5,812,629 and 7,180,979, for example).

U.S. Pat. No. 7,180,979 discloses an X ray imaging apparatus that utilizes a Talbot interferometer constituted by an X ray source, two diffraction gratings, and an X ray image detector.

Japanese Unexamined Patent Publication No. 2006-259264 discloses production of an amplitude diffraction grating by forming deep grooves in resin using X ray lithography.

Japanese Unexamined Patent Publication No. 2007-203063 discloses an X ray apparatus equipped with detection elements which are constituted by a multiplicity of elongate detection strips. This X ray apparatus enables obtainment of phase images by single measurement using each beam, and the number of measurements necessary to obtain phase images can be reduced.

It is necessary to provide two diffraction gratings of sizes equivalent to that of a subject in the X ray imaging apparatus disclosed in U.S. Pat. No. 7,180,979, which is costly. In addition, of the two diffraction gratings, it is desirable for the one toward the X ray image detector to be an amplitude diffraction grating. In this case, it is necessary to produce a diffraction grating having an extremely high aspect ratio and metallic diffraction members at fine pitches. As an example, the width of the diffraction members of such a diffraction grating is 2 μm to 10 μm, and the thickness thereof is 25 μm to 100 μm. It is necessary to employ a special manufacturing method such as that disclosed in Japanese Unexamined Patent Publication No. 2006-259264 in order to produce such a diffraction grating, and it is difficult to produce diffraction gratings having uniform structures.

In the case that a multiplicity of elongate detection strips are provided as in the X ray apparatus disclosed in Japanese Unexamined Patent Publication No. 2007-203063, it is necessary to form the width of each detection strip to be thinner as the number of phase component images taken simultaneously increases. This is also difficult to realize from a manufacturing standpoint.

SUMMARY OF THE INVENTION

The present invention has been developed in view of the foregoing circumstances. It is an object of the present invention to provide a phase contrast radiation imaging apparatus having a simpler structure and is therefore easier to manufacture. It is another object of the present invention to provide a radiation image detector to be employed by the phase contrast radiation imaging apparatus.

A radiation image detector of the present invention comprises:

a charge generating layer that generates electric charges when radiation bearing a radiation image is irradiated thereon; and charge collecting electrodes that collect the electric charges which are generated in the charge generating layer;

the charge collecting electrodes being constituted by a plurality of linear electrode groups, which are electrically independent from each other;

the linear electrode groups being constituted by a plurality of linear electrodes, which are arranged at a constant period and electrically connected to each other; and the plurality of linear electrode groups being provided such that the phases thereof are different.

The plurality of linear electrode groups may be arranged to form two or three pairs of linear electrode groups, which are arranged alternately such that the phase of the arrangement period thereof are opposite each other.

The lengths of the linear electrodes of the pairs of linear electrode groups may be greater than the widths of the pairs of linear electrode groups in a direction perpendicular to the length directions thereof.

The radiation detector of the present invention may further comprise:

constant potential linear electrodes, which are provided to surround each of the pairs of linear electrode groups and have substantially the same electrical potential as the charge collecting electrodes.

The radiation detector of the present invention may further comprise:

constant potential linear electrodes, which are provided to surround the pairs of the plurality of linear electrode groups that correspond to each of the pixel units that constitute the radiation image and have substantially the same electrical potential as the pairs of the plurality of linear electrode groups.

A phase contrast radiation imaging apparatus of the present invention comprises:

a radiation source;

a diffraction grating, into which radiation emitted from the radiation source enters; and a radiation image detector defined in Claim 1, onto which the radiation which has passed through the diffraction grating is irradiated;

the diffraction grating being configured such that Talbot's effect is generated when radiation is irradiated thereon; and the radiation image detector detecting signals that correspond to phase components.

At least the radiation image detector, from among the diffraction grating and the radiation image detector, may be formed along an arcuate surface, which has a line that passes through the radiation source and extends in the longitudinal direction of diffraction members of the diffraction grating as its central axis.

The diffraction grating may be a phase diffraction grating; and the diffraction grating may project an image of grating fringes having equidistant intervals therebetween onto the arcuate surface.

The diffraction grating may be formed along an arcuate surface, which has a line that passes through the radiation source and extends in the longitudinal direction of the diffraction member of the diffraction grating as its central axis.

Phase components, which are necessary to form a phase image, may be obtained without moving the diffraction grating and the radiation image detector relative to each other when detecting the signals that correspond to the phase components.

The phase contrast radiation imaging apparatus of the present invention may further comprise:

a radiation image output section that administers image processes onto image data, which are obtained based on period data detected by the radiation image detector, such that the image data represents a radiation image formed by radiation which has been diffracted by the diffraction grating and projected onto a planar surface, and outputs the processed image data.

The phase contrast radiation imaging apparatus of the present invention may further comprise:

a moving mechanism that moves the radiation source, the diffraction grating and the radiation image detector integrally with respect to a subject which is placed between the radiation source and the radiation image detector; and an image constructing section that constructs desired tomographic images or a three dimensional image of the subject, based on a plurality of sets of image data which are detected by the radiation image detector during movement thereof by the moving mechanism.

In the radiation image detector of the present invention, the linear electrode groups are constituted by a plurality of linear electrodes, which are arranged at a constant period and electrically connected to each other; and the plurality of linear electrode groups are provided such that the phases thereof are different. Therefore, if the radiation image detector is employed in a phase contrast radiation imaging apparatus that utilizes a Talbot interferometer, it is not necessary to provide an amplitude diffraction grating as in conventional phase contrast radiation imaging apparatuses. Therefore, the apparatus becomes simple in structure, manufacture thereof is facilitated, and costs can be reduced.

Further, the plurality of linear electrode groups can obtain image signals for a plurality of phase components by a single imaging operation.

The plurality of linear electrode groups may be arranged to form two or three pairs of linear electrode groups, which are arranged alternately such that the phase of the arrangement period thereof are opposite each other. In this case, image signals for at least four phase components can be obtained by a single imaging operation. In addition, if two or three of the pairs of linear electrode groups are provided in a plane, it is not necessary to form the widths of the linear electrodes to be narrow, unlike linear electrodes for obtaining data corresponding to four or six phase components, which are sequentially provided (refer to FIG. 11 for the configuration of linear electrode groups capable of obtaining data corresponding to six phase components).

The lengths of the linear electrodes of the pairs of linear electrode groups may be greater than the widths of the pairs of linear electrode groups in a direction perpendicular to the length directions thereof. In this case, the area within the linear electrode groups occupied by the connecting portions of the linear electrodes is relatively decreased. Therefore, the size of an effective detection surface for image formation can be made great, which is advantageous.

The radiation detector of the present invention may further comprise the constant potential linear electrodes, which are provided to surround each of the pairs of linear electrode groups and have substantially the same electrical potential as the charge collecting electrodes. The radiation detector of the present invention may further comprise constant potential linear electrodes, which are provided to surround the pairs of the plurality of linear electrode groups that correspond to each of the pixel units that constitute the radiation image and have substantially the same electrical potential as the pairs of the plurality of linear electrode groups. In these cases, the electric fields which are generated within the charge generating layer by the linear electrodes can be stabilized, thereby preventing contamination of the phase components, to be described later.

The phase contrast radiation imaging apparatus of the present invention comprises: a radiation source; a diffraction grating, into which radiation emitted from the radiation source enters; and a radiation image detector defined in Claim 1, onto which the radiation which has passed through the diffraction grating is irradiated. The diffraction grating is configured such that Talbot's effect is generated when radiation is irradiated thereon, and the radiation image detector detects signals that correspond to phase components. Therefore, a phase contrast radiation imaging apparatus can be constituted without providing an amplitude diffraction grating as in conventional phase contrast radiation imaging apparatuses. Accordingly, the structure of the apparatus is simplified, manufacture thereof is facilitated, and costs can be reduced.

At least the radiation image detector, from among the diffraction grating and the radiation image detector, may be formed along an arcuate surface, which has a line that passes through the radiation source and extends in the longitudinal direction of diffraction members of the diffraction grating as its central axis. In this case, the conditions for the Talbot effect can be satisfied at portions other than the central portions of the diffraction grating and the radiation image detector. Accordingly, large sized phase contrast imaging becomes possible. In addition, manufacture of the apparatus is simpler than in cases in which diffraction gratings are formed in spherical shapes.

The diffraction grating may be a phase diffraction grating; and the diffraction grating may project an image of grating fringes having equidistant intervals therebetween onto the arcuate surface. In this case, it is not necessary to form the diffraction grating along an arcuate surface. Manufacture of the diffraction grating becomes easier, particularly in cases that the diffraction grating is formed on a flat plane.

The diffraction grating may be formed along an arcuate surface, which has a line that passes through the radiation source and extends in the longitudinal direction of the diffraction member of the diffraction grating as its central axis. In this case, it becomes possible to employ an amplitude diffraction grating. In systems in which the amplitude diffraction grating is placed between subjects and radiation sources, the radiation dosage can be reduced, and improvements in contrast can be expected.

The plurality of linear electrode groups may be arranged to form at least two pairs of linear electrode groups, which are arranged alternately such that the phase of the arrangement period thereof are opposite each other. In this case, image signals corresponding to at least four phase components can be obtained with a single imaging operation. That is, phase components, which are necessary to form a phase image, can be obtained without moving the diffraction grating and the radiation image detector relative to each other.

Image processes may be administered onto image data, which are obtained based on phase component images detected by the radiation image detector, such that the image data represents a conventional radiation image formed by radiation which has been diffracted by the diffraction grating and projected onto a planar surface. Then, the processed image data may be output. In this case, the obtained phase contrast radiation image approaches a radiation image obtained by a conventional planar radiation image detector.

Therefore, physicians are enabled to perform diagnosis using radiation images that are similar in shape to those that they are familiar with.

The radiation source, the diffraction grating and the radiation image detector may be moved integrally with respect to a subject which is placed between the radiation source and the radiation image detector, and desired tomographic images or a three dimensional image of the subject may be constructed, based on a plurality of sets of image data which are detected by the radiation image detector during movement thereof. In this case, application to a phase contrast radiation tomosynthesis apparatus or a phase contrast radiation CT apparatus becomes possible.

BRIEF DESCRIPTION OF THE DRAWINGS

FIG. 6 is a sectional view of the detection element, taken along line 6-6 of FIG. 5.

FIG. 7 is a sectional view of the detection element, taken along line 7-7 of FIG. 5.

FIG. 19 is a diagram for explaining the construction of linear electrodes of the radiation image detector employed by the phase contrast radiation imaging apparatus of the second embodiment of the present invention.

DESCRIPTION OF THE PREFERRED EMBODIMENTS

Figure 1:
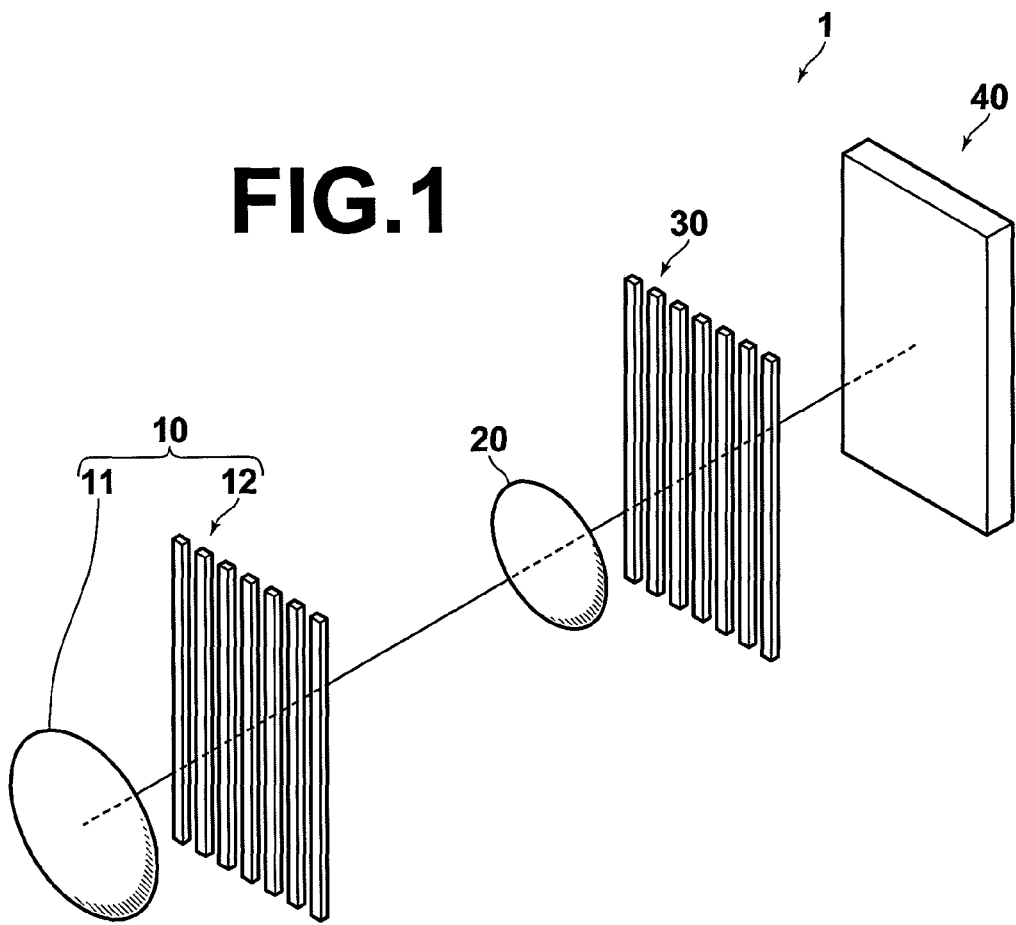
FIG. 1 is a diagram that illustrates the schematic construction of a phase contrast radiation imaging apparatus according to a first embodiment and a second embodiment of the present invention.

Hereinafter, a first embodiment of a phase contrast radiation imaging apparatus that employs the radiation image detector of the present invention will be described with reference to the attached drawings. The phase contrast radiation imaging apparatus of the first embodiment employs a radiation image detector of the TFT readout type. FIG. 1 is a diagram that illustrates the schematic construction of the phase contrast radiation imaging apparatus 1.

As illustrated in FIG. 1, the phase contrast radiation imaging apparatus 1 is equipped with: a radiation irradiating section 10, for emitting radiation toward a subject 20; a diffraction grating 30, onto which radiation emitted from the radiation irradiating source 10 and has passed through the subject 20 is irradiated; and a radiation image detector 40 for detecting the radiation diffracted by the diffraction grating 30.

As illustrated in FIG. 1, the radiation irradiating section 10 is equipped with a radiation source 11 that emits radiation, and a multi slit 12, through which radiation emitted from the radiation source 11 passes. The detailed construction of the radiation irradiating section 10 is described in F. Pfeiffer et al., "Phase retrieval and differential phase-contrast imaging with low-brilliance X-ray sources", Nature Physics Letters, Vol. 2, No. 1, pp. 258-261, 2006, for example.

Figure 2:
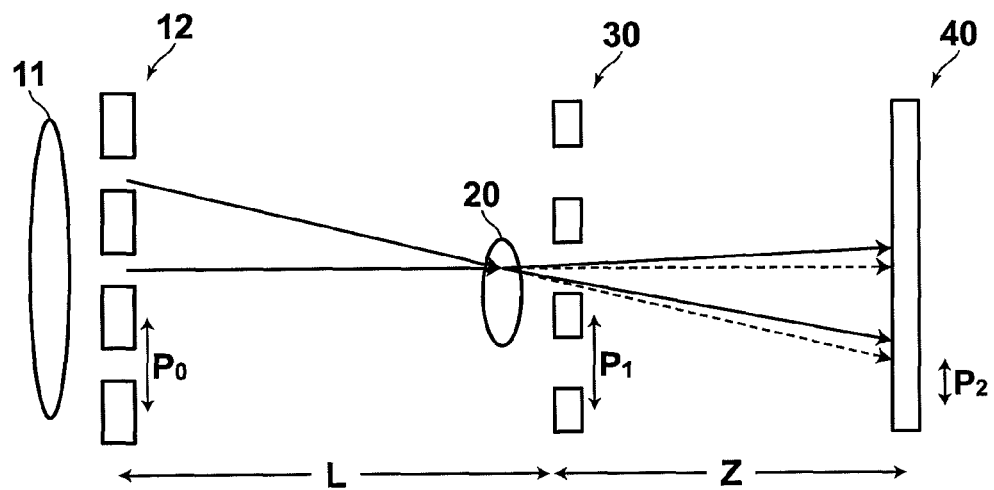
FIG. 2 illustrates the positional relationship among the constituent elements of the phase contrast radiation imaging apparatus of FIG. 1.

FIG. 2 illustrates the positional relationship among the constituent elements of the phase contrast radiation imaging apparatus 1.

It is necessary for the pitch $P_0$, at which the slits of the multi slit 12 are provided, to satisfy the following equation:

$$P_0 = P_2 \times L/Z$$

Note that $P_2$ is the pitch at which linear electrodes of the radiation image detector 40 are provided. The details of the radiation image detector 40 will be described later.

The radiation irradiating section 10 is not limited to the configuration described above, and a micro focus X ray tube may be utilized. As a further alternative, a combination of a micro focus X ray tube and the aforementioned micro slit may be used.

As a still further alternative, the plasma X ray source disclosed in L. M. Chen et al., "Phase-contrast x-ray imaging with intense Ar Kα radiation from femtosecond-laser-driven gas target", Applied Physics Letters, Vol. 90, No. 211501, 2007. This plasma X ray source can be focused to an extremely small focal spot size (12 µm, for example), and therefore, the multi slit 12 becomes unnecessary.

Figure 3:
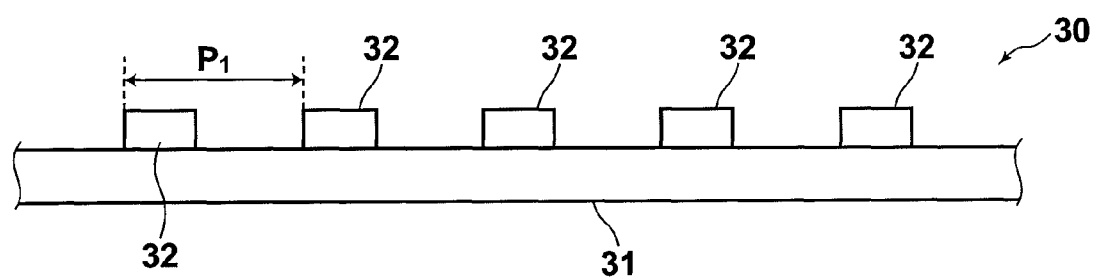
FIG. 3 is a diagram that schematically illustrates a diffraction grating.

As illustrated in FIG. 3, the diffraction grating 30 is equipped with a substrate 31, and a plurality of diffraction members 32 which are attached to the substrate 31. The substrate 31 may be formed by glass, for example. All of the plurality of diffraction members 32 are linear, and extend unidirectionally (the direction perpendicular to the drawing sheet of FIG. 3). The pitch $P_1$ at which the diffraction members 32 are provided is constant in the first embodiment.

The phase contrast radiation imaging apparatus of the first embodiment obtains phase contrast radiation data of the subject, utilizing the Talbot effect which is generated at the diffraction grating 30. For this to occur, the placement of the diffraction grating 30 and the pitch $P_1$ (that is, the period of the diffraction grating) at which the diffraction members 32 are provided must be set to satisfy the following equation:

$$Z = (m+1/2)P_1^2/\lambda$$

Here, m is either 0 or a positive integer, and λ is the wavelength of the radiation.

Gold, for example, may be employed as the material of the diffraction members 32 of the diffraction grating 30. It is preferable for the diffraction members 32 to be those that constitute a so called phase diffraction grating, by which phase modulation of approximately 80° to 100° (more preferably 90°) is imparted onto the radiation irradiated thereon. That is, the diffraction members 32 vary the phase velocity of the radiation irradiated thereon.

Figure 4:
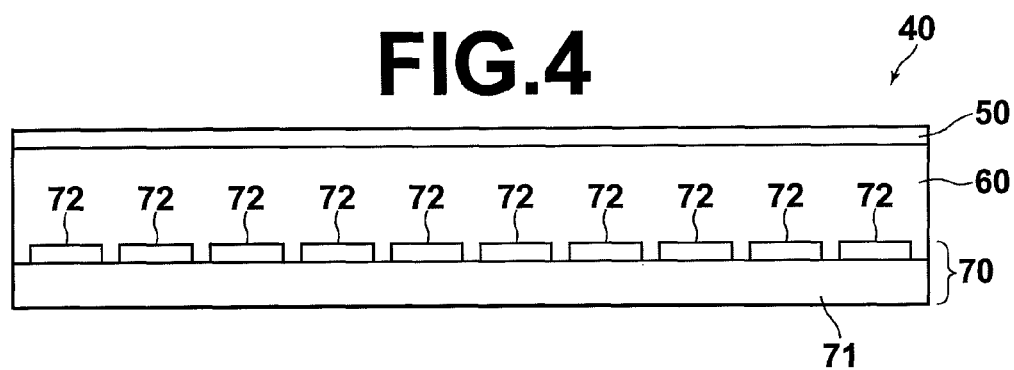
FIG. 4 is a partial sectional view that schematically illustrates a radiation image detector, which is used in phase contrast radiation imaging apparatuses according to the first embodiment and a third embodiment.

Next, the radiation image detector 40 of the phase contrast radiation imaging apparatus 1 of the first embodiment will be described in detail. FIG. 4 is a partial sectional view of the radiation image detector 40.

As illustrated in FIG. 4, the radiation image detector 40 is equipped with: an active matrix substrate 70; a semiconductor layer 60 which is laminated on the active matrix substrate 70 to cover the entire surface thereof; and an upper electrode 50.

The semiconductor layer 60 has electromagnetic wave conductivity, and generates charges therein when X rays are irradiated thereon. A 100 µm to 1500 µm thick amorphous Se film having selenium as its main component may be employed as the semiconductor layer 60. However, the material of the semiconductor layer 60 is not limited to amorphous Se. Other possible materials include: $PbI_2$; $HgI_2$; $Cd(Zn)Te$; $Bi_{12}TiO_{20}$; $Bi_{12}SiO_{20}$; and $Bi_{12}GeO_{20}$. The semiconductor layer 60 is formed on the active matrix substrate 70 by the vacuum vapor deposition method or the like.

The upper electrode 50 is constituted by a low resistance conductive material, such as Au and Al, and is of a thickness that transmits radiation irradiated thereon. Note that intermediate layers may be provided between the upper electrode 50 and the semiconductor layer 60. Examples of such intermediate layers include: a charge transport layer, for preventing charge injection from the upper electrode 50 while enabling electric charges having a polarity opposite that of the injected electric charges to reach the upper electrode 50; and a crystallization preventing layer, for preventing crystallization of the amorphous Se.

As illustrated in FIG. 4, the active matrix substrate 70 is constituted by a great number of unit elements 72 that correspond to pixels of the radiation image of the subject, which are two dimensionally arranged on the glass substrate 71. Each unit element 72 includes: a collecting electrode; a switching element; and the like.

Figure 5:
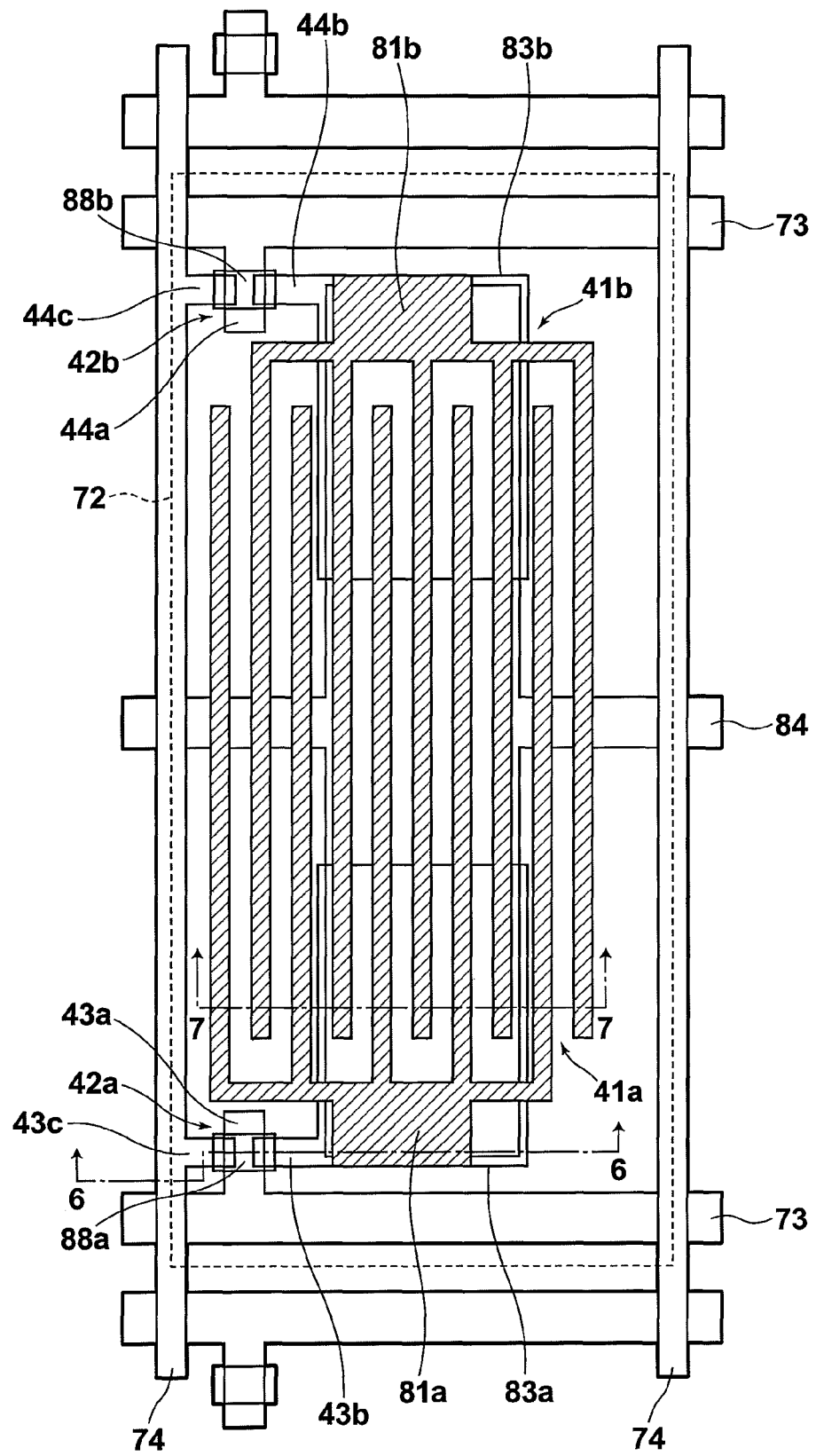
FIG. 5 is a plan view that illustrates a detection element on an active matrix.

Here, the details of the structure for each pixel unit or for each sub pixel unit of the radiation image detector 40 will be described. Note that in the first embodiment, the term "sub pixel" refers to a pair of linear electrode groups which are alternately arranged such that the phases of their arrangement periods are opposite each other. FIG. 5 is a plan view of the radiation image detector 40. FIG. 6 is a sectional view of the radiation image detector 40 taken along line 6-6 of FIG. 5. FIG. 7 is a sectional view of the radiation detector 40 taken along line 7-7 of FIG. 5.

Each unit element 72 of the radiation image detector 40 is equipped with: charge collecting electrodes, which are constituted by a first linear electrode group 81a and a second linear electrode group 81b, for collecting electric charges which are generated in the semiconductor layer 60; a first accumulating capacitor 41a, for accumulating electric charges which are collected by the first linear electrode group 81a; a second accumulating capacitor 41b, for accumulating electric charges which are collected by the second linear electrode group 81b; a first TFT switch 42a for reading out the electric charges accumulated in the first accumulating capacitor 41a; and a second TFT switch 42b for reading out the electric charges accumulated in the second accumulating capacitor 41b.

Figure 8:
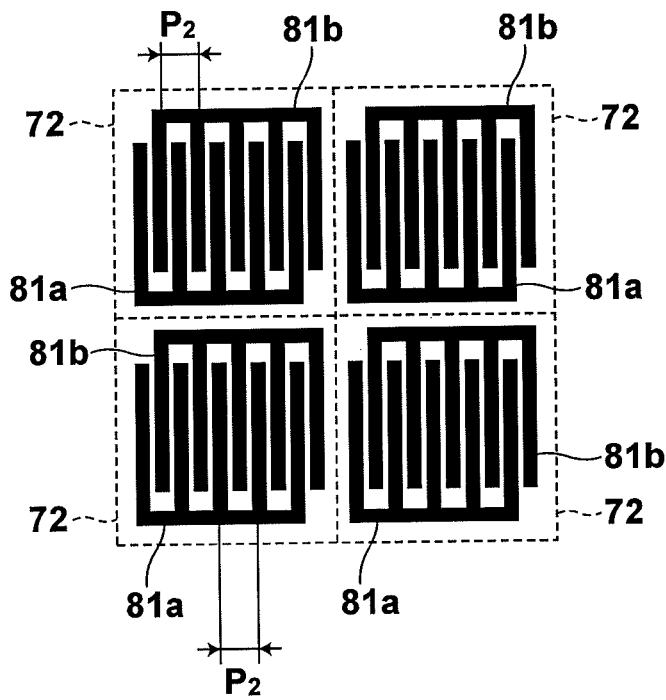
FIG. 8 is a diagram that schematically illustrates first linear electrode groups and second linear electrode groups for detection elements corresponding to four pixels.

FIG. 8 is a diagram that schematically illustrates the first linear electrode groups 81a and the second linear electrode groups 81b for unit elements 72 corresponding to four pixels. The first linear electrode groups 81a and the second linear electrode groups 81b are each constituted by a multiplicity of linear electrodes, which are arranged periodically at a pitch $P_2$. The first linear electrode groups 81a and the second linear electrode groups 81b are formed such that the linear electrodes of the second electrode groups 81b are positioned between the linear electrodes of the first electrode groups 81a. The first linear electrode groups 81a and the second linear electrode groups 81b are also formed such that the phase of the arrangement period of the first linear electrode groups 81a and the phase of the arrangement period of the second linear electrode groups 81b are shifted by π (180°, corresponding to half the pitch). In addition, as illustrated in FIG. 8, the linear electrodes of the linear electrode groups 81a are electrically connected to each other, and the linear electrodes of the linear electrode groups 81b are electrically connected to each other. Note that it is desirable for the lines that connect the linear electrodes to be provided in a plane different from that of the linear electrodes, such that these lines do not function as electrodes themselves. However, if the widths of the lines that connect the linear electrodes are narrow, the influence exerted thereby can be suppressed to levels that can be ignored.

The pitch $P_2$, at which the linear electrodes of the first electrode groups 81a are arranged, and the pitch $P_2$, at which the linear electrodes of the second electrode groups 81b are arranged, are within a range from 2 μm to 15 μm. Note that as described above, the size of the arrangement pitch $P_2$ is one of the conditions that determine the slit pitch $P_0$, at which the slits of the multi slit 12 are provided. Note also that the widths of each of the linear electrodes of the first linear electrode groups 81a and the widths of each of the linear electrodes of the second linear electrode groups 81b are within a range from 1 μm to 14 μm.

The first linear electrode groups 81a and the second linear electrode groups 81b may be formed by amorphous transparent conductive oxide films.

Intermediate layers may be provided between the first linear electrode groups 81a and the second linear electrode groups 81b, and the semiconductor layer 60. Examples of such intermediate layers include: a charge transport layer, for preventing charge injection from the linear electrodes while enabling electric charges having a polarity opposite of the injected charges generated within the semiconductor layer 60 to reach the first linear electrode groups 81a and the second linear electrode groups 81b; and a crystallization preventing layer, for preventing crystallization of the amorphous Se.

Each of the first accumulating capacitors 41a is constituted by: a connecting electrode 83a; a gate insulative film 85; and a charge accumulating capacitor electrode 84. The gate insulative film 85 functions as a dielectric, and electric charges are accumulated between the connecting electrode 83a and the charge accumulating capacitor electrode 84. Each of the second accumulating capacitors 41b is constituted by: a connecting electrode 83b; a gate insulative film 85; and a charge accumulating capacitor electrode 84. The gate insulative film 85 functions as a dielectric, and electric charges are accumulated between the connecting electrode 83b and the charge accumulating capacitor electrode 84.

Each of the first TFT switches 42a includes: a gate electrode 43a, which is formed by being drawn from a scanning line 73 to be described later; a drain electrode 43b, which is formed by being drawn from the connecting electrode 83a; a source electrode 43c, which is formed by being drawn from a data line 74 to be described later; a gate insulative film 85 and a semiconductor film 88a. Each of the second TFT switches 42b includes: a gate electrode 44a, which is formed by being drawn from the scanning line 73; a drain electrode 44b, which is formed by being drawn from the connecting electrode 83a; a source electrode 44c, which is formed by being drawn from the data line 74; the gate insulative film 85 and a semiconductor film 88b. The gate insulative film 85 may be formed by $SiN_x$ or $SiO_x$, for example. The semiconductor films 88a and 88b are channel portions of the first and second TFT switches 42a and 42b. The semiconductor films 88a and 88b are paths for current that connect the data lines 74 and the connecting electrodes 83a and 83b.

Insulating protective films 87 are formed to cover the first accumulating capacitors 41a, the second accumulating capacitors 41b, the first TFT switches 42a, the second TFT switches 52b, and the data lines 74. Contact holes 86 are formed in the insulating protective films 87 at connecting portions between the first linear electrode groups 81a and the connecting electrodes 83a, and at connecting portions between the second linear electrode groups 81b and the connecting electrodes 83b.

An interlayer insulative film 82 is formed on the upper surfaces of the insulating protective films 87. The contact holes 86 penetrate through the interlayer insulative film 82. The first linear electrode groups 81a and the connecting electrodes 83a are connected via the contact holes 86. The second linear electrode groups 81b and the connecting electrodes 83b are also connected via the contact holes 86. The interlayer insulative film 82 is an organic insulative film, and function to insulate and electrically separate the first and second TFT switches 42a and 42b from each other. Acrylic resin may be employed as the material of the organic insulative film, for example.

As illustrated in FIG. 5, the scanning lines 73 and the data lines 74 are electrode wires which are arranged as a grid. The first TFT switches 42a and the second TFT switches 42b are formed in the vicinities of the intersections between the scanning lines 73 and the data lines 74. Different scanning lines 73 are connected to the first TFT switches 42a and the second TFT switches 42b. The first TFT switches 42a and the second TFT switches 42b are configured such that ON/OFF operations thereof are controlled independently.

Readout circuits (now shown) including an amplifier for detecting signal charges which flow through the data lines 74 are connected to the ends of the data lines 74. Gate drivers (not shown) that output control signals to turn the first TFT switches 42a and the second TFT switches 42b ON/OFF independently are connected to the scanning lines 73.

Next, the operation by which the phase contrast radiation imaging apparatus of the first embodiment records a radiation image onto the radiation image detector, and the operation by which the radiation image is read out, will be described.

First, the subject 20 is placed between the radiation irradiating section 10 and the diffraction grating 30 (refer to FIG. 1). Note that the subject 20 is placed between the radiation irradiating section 10 and the diffraction grating 30 in the phase contrast radiation imaging apparatus of the first embodiment. Alternatively, the subject 20 may be placed between the diffraction grating 30 and the radiation image detector 40. In this case, the distance between the subject 20 and the radiation image detector 40 becomes smaller, and the magnification rate also decreases. Therefore, installation of the phase contrast radiation imaging apparatus in existing radiation imaging rooms is facilitated.

Radiation is emitted from the radiation source 11 of the radiation irradiating section 10. The radiation passes through the multi slit 12 and is irradiated onto the subject 20. Then, the radiation passes through the subject 20 and is irradiated onto the diffraction grating 30. Thereafter, the radiation passes through the diffraction grating 30. At this time, the Talbot effect occurs at the diffraction grating 30. The Talbot effect is a phenomenon in which a self image of a diffraction grating is formed at the aforementioned distance Z when planar waves pass through the diffraction grating, in the case that the diffraction grating is a phase diffraction grating. In the case described above, the phase of the radiation is shifted because it has passed through the subject 20. Therefore, the wave front of the radiation that enters the diffraction grating 30 is distorted. Accordingly, the self image of the diffraction grating 30 is also deformed.

The radiation that bears the self image formed by the Talbot effect of the diffraction grating 30 is irradiated onto the radiation image detector 40 from the side of the upper electrode 50, in a state in which a voltage source is applying positive voltage to the upper electrode 50. Note that in the phase contrast radiation imaging apparatus 1 of the first embodiment, the radiation image detector 40 is placed such that the upper electrode 50 faces the radiation irradiating section. In addition, the longitudinal directions of the linear electrodes of the first and second linear electrode groups 81a and 81b are the same as the longitudinal directions of the diffraction members 32 of the diffraction grating 30.

The radiation which is irradiated onto the radiation image detector 40 passes through the upper electrode 50 and enters the semiconductor layer 60. The radiation causes charge pairs to be generated within the semiconductor layer 60. Negative electric charges from among the charge pairs combine with the positive charges charged on the upper electrode 50 and disappear, while positive electric charges are collected by the first and second linear electrode groups 81a and 81b for each unit element 72, and accumulated in the first and second accumulating capacitors 41a and 41b.

Figure 9:
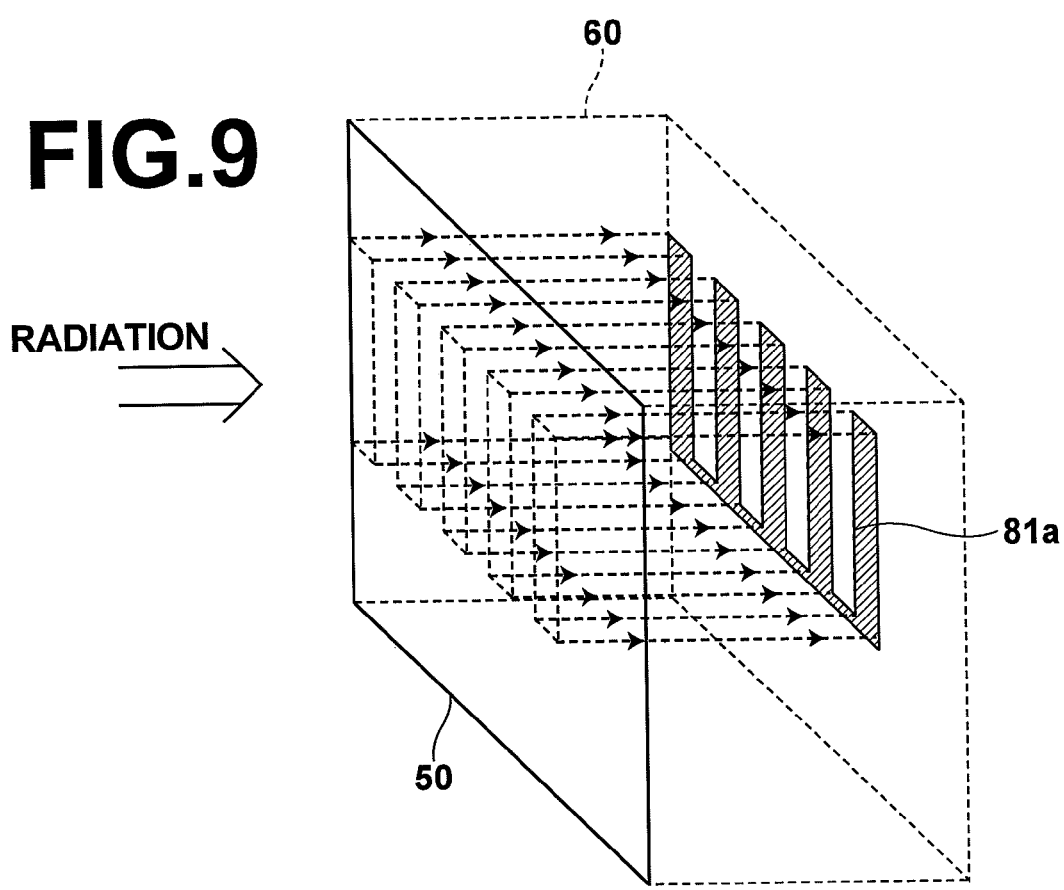
FIG. 9 illustrates electric fields, which are formed within a semiconductor layer by the first linear electrode groups.

In the radiation image detector 40 of the phase contrast radiation imaging apparatus, the charge collecting electrodes that collect the electric charges generated in the semiconductor layer 60 are constituted by the first linear electrode groups 81a and the second linear electrode groups 81b. Accordingly, when the voltage is applied to the upper electrode 50 as described above, electric fields which are parallel to the linear electrodes of the first and second linear electrode groups 81a and 81b, that is, perpendicular to the surface of the upper electrode 50, are formed, as illustrated in FIG. 9. The electric charges which are generated within the semiconductor layer 60 travel along the electric fields without being dispersed, and are collected by the first and second linear electrode groups 81a and 81b. Therefore, the first and second linear electrode groups 81a and 81b perform substantially equivalent functions as a combination of an amplitude diffraction grating and a detector. Accordingly, electric charges that represent image contrast generated by a combination of the deformed self image of the diffraction grating 30 and the practical diffraction grating formed by the first linear electrode groups 81a are accumulated in the first accumulating capacitors 41a. Likewise, electric charges that represent image contrast generated by a combination of the deformed self image of the diffraction grating 30 and the practical diffraction grating formed by the second linear electrode groups 81b are accumulated in the second accumulating capacitors 41b. The image contrast is generally represented as Moire fringes. As described above, the phases of the first linear electrode groups 81a and the second linear electrode groups 81b are shifted by $\pi$. Therefore, signals that correspond to two types of phase components, of which the phases are shifted by $\pi$, are detected by the radiation image detector 40.

Next, the gate drivers (not shown) sequentially output control signals that turn the first TFT switches 42a ON to each of the scanning lines 73 which are connected to the first TFT switches 42a. The first TFT switches 42a are turned ON in response to the control signals, and the electric charges which are accumulated in the first accumulating capacitors 41a of each unit element 72 are read out by the data lines 74 thereof. The electric charge signals 74 that flow through the data lines 74 are detected by charge amplifiers of the readout circuits, as image signals that correspond to first phase components.

Thereafter, the gate drivers (not shown) sequentially output control signals that turn the second TFT switches 42b ON to each of the scanning lines 73 which are connected to the second TFT switches 42b. The second TFT switches 42b are turned ON in response to the control signals, and the electric charges which are accumulated in the second accumulating capacitors 41b of each unit element 72 are read out by the data lines 74 thereof. The electric charge signals 74 that flow through the data lines 74 are detected by charge amplifiers of the readout circuits, as image signals that correspond to second phase components.

Here, the Moire fringes generated as described above are modulated by the subject 20. The amount of modulation is proportional to an angle at which the radiation is bent, due to the refracting effect of the subject 20. Accordingly, the subject 20 and the inner structure thereof can be detected, by analyzing the image signals corresponding to the first phase components and the image signals corresponding to the second phase components which are detected by the radiation image detector 40.

Next, modifications of the radiation image detector 40 of the phase contrast radiation imaging apparatus of the first embodiment will be described.

Figure 10:
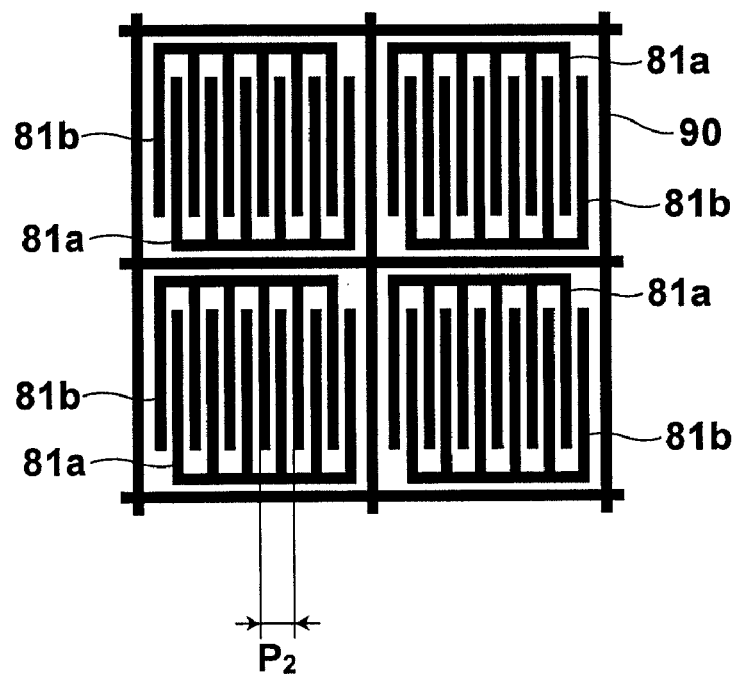
FIG. 10 is a diagram that illustrates a modification to the radiation image detector employed by the phase contrast radiation imaging apparatus of the first embodiment.

As illustrated in FIG. 10, constant potential linear electrodes 90 may be provided in a grid pattern to surround the first linear electrode groups 81a and the second linear electrode groups 81b of each unit element 72. If there are gaps among the charge collecting electrodes, electric fields will be bent, electric charges will gather at portions where linear electrodes are not present, and contamination of the phase components will occur. Therefore, by providing the constant potential linear electrodes 90 as described above, the electric fields can be stabilized, and the occurrence of such contamination can be prevented. Electric potentials are applied to the constant potential linear electrodes 90 such that electric potential differences among the surrounding charge collecting electrodes do not become great. That is, the electric potentials of the constant potential linear electrodes 90 are approximately the same as those of the charge collecting electrodes. More specifically, electric potentials equal to a grounded state or that approach a grounded state are applied. Note that in the case that the constant potential linear electrodes 90 are provided, it is desirable for the first linear electrode groups 81a and the second linear electrode groups 81b to be of the configuration and arrangement illustrated in FIG. 10.

In addition, in the radiation image detector 40 of the first embodiment, the first linear electrode groups 81a and the second linear electrode groups 81b were provided as charge collecting electrodes for each unit element 72. The phases of the first linear electrode groups 81a and the second linear electrode groups 81b were shifted by $\pi$. However, the shapes of the charge collecting electrodes is not limited to such a configuration.

Figure 11:
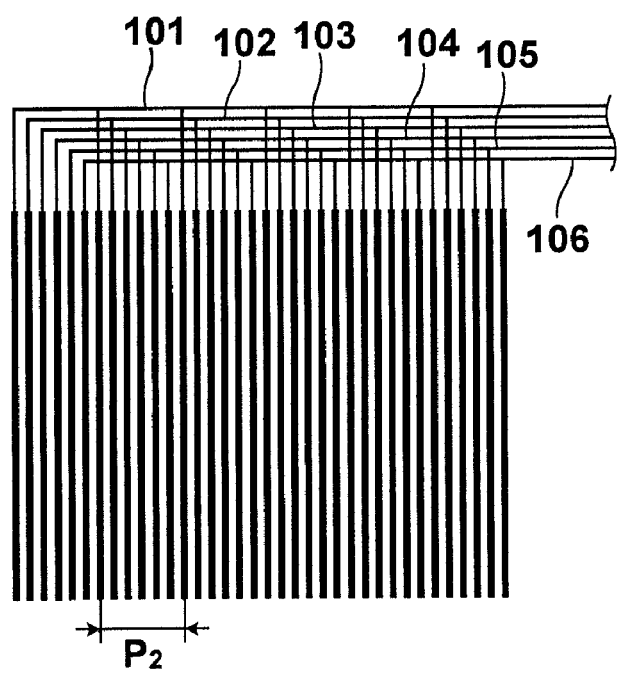
FIG. 11 is a diagram that illustrates a modification to the radiation image detector employed by the phase contrast radiation imaging apparatus of the first embodiment.

For example, first through sixth linear electrode groups 101 through 106, in which linear electrodes are arranged at a pitch $P_2$, may be provided with the phases in the arrangement periods thereof being shifted by $\pi/3$, as illustrated in FIG. 11. Specifically, if the phase of the first linear electrode group 101 is designated as 0, the phase of the second linear electrode group 102 is $\pi/3$, the phase of the third linear electrode group 103 is $2\pi/3$, the phase of the fourth linear electrode group 104 is $\pi$, the phase of the fifth linear electrode group 105 is $4\pi/3$, and the phase of the sixth linear electrode group 106 is $5\pi/3$.

Image signals corresponding to six different phase components can be obtained with a single radiation imaging operation, by configuring the charge collecting electrodes as illustrated in FIG. 11. In this case, the electric charges collected by the first through sixth linear electrode groups 101 through 106 are read out for each linear electrode group.

Figure 12:
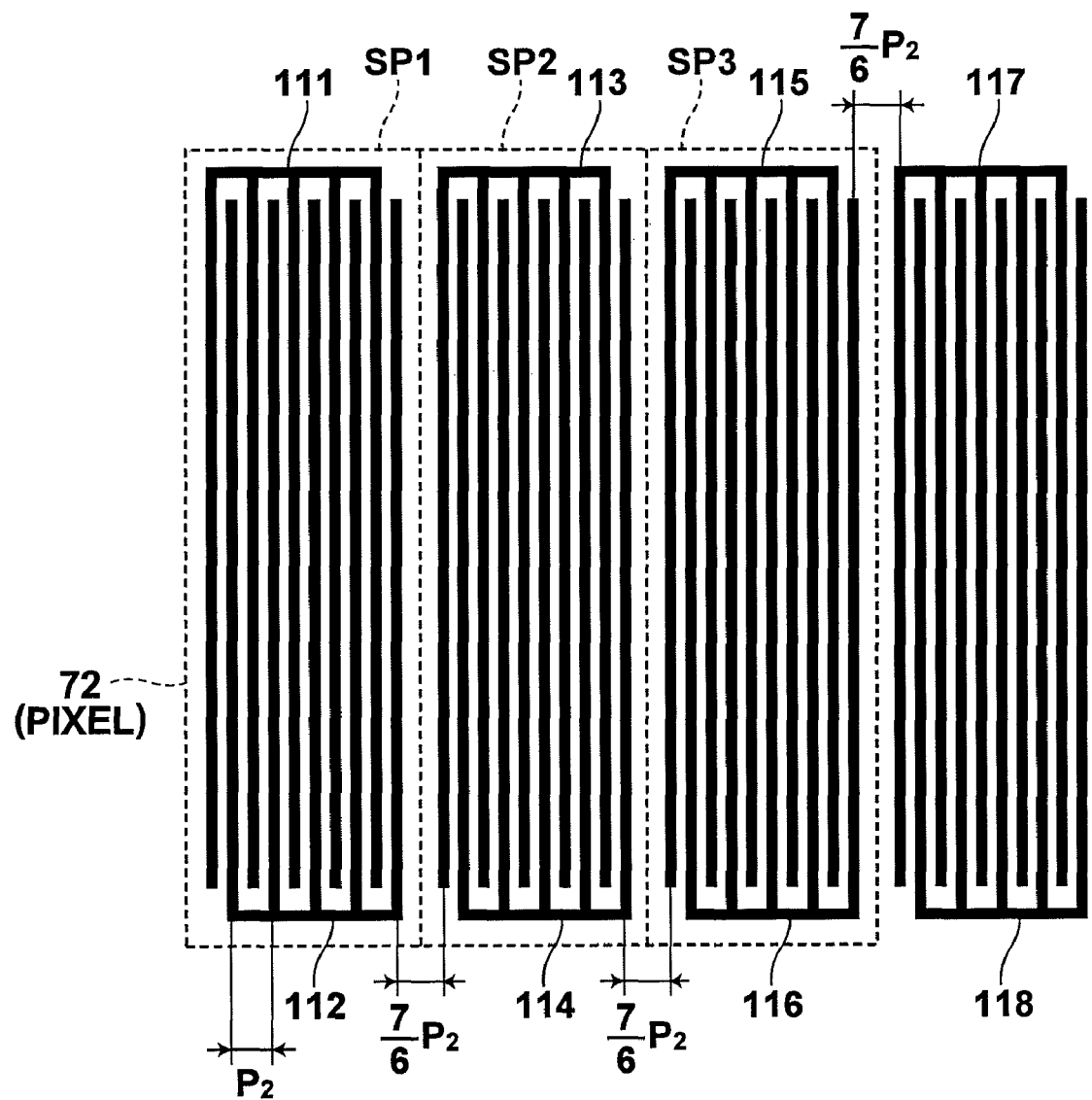
FIG. 12 is a diagram that illustrates a modification to the radiation image detector employed by the phase contrast radiation imaging apparatus of the first embodiment.

Alternatively, as a pixel corresponding to a single unit element 72 may be sectioned into a plurality of sub pixels (three in the example of FIG. 12), as illustrated in FIG. 12. Linear electrode groups having different phases may be provided in each sub pixel region. Note that the sub pixels refers to pairs of linear electrode groups which are alternately arranged such that the phases of their arrangement periods are opposite each other. Specifically, in the modification illustrated in FIG. 12, a first linear electrode group 111 and a second linear electrode group 112, in which linear electrodes are arranged at a pitch $P_2$, are provided such that the phases thereof are shifted by π, within a sub pixel SP1. Likewise, a third linear electrode group 113 and a fourth linear electrode group 114, in which linear electrodes are arranged at a pitch $P_2$, are provided such that the phases thereof are shifted by π, within a sub pixel SP2. A fifth linear electrode group 115 and a sixth linear electrode group 116, in which linear electrodes are arranged at a pitch $P_2$, are provided such that the phases thereof are shifted by π, within a sub pixel SP3. Adjacent linear electrode groups of the sub pixel SP1 and the sub pixel SP2 are separated by a pitch (7/6)·$P_2$, and adjacent linear electrode groups of the sub pixel SP2 and the sub pixel SP3 are separated by a pitch (7/6)·$P_2$. Thereby, the phases are shifted 4π/3 among the sub pixels. By providing the linear electrode groups within a single pixel as illustrated in FIG. 12, if the phase of the first linear electrode group 111 is designated as 0, the phase of the second linear electrode group 112 is π, the phase of the third linear electrode group 113 is 4π/3, the phase of the fourth linear electrode group 114 is π/3, the phase of the fifth linear electrode group 115 is 2π/3, and the phase of the sixth linear electrode group 116 is 5π/3. Note that linear electrode groups 117 and 118 are linear electrode groups of an adjacent pixel.

Image signals corresponding to six different phase components can be obtained with a single radiation imaging operation, by configuring the charge collecting electrodes as illustrated in FIG. 12. In this case, the electric charges collected by the first through sixth linear electrode groups 111 through 116 are read out for each linear electrode group. Image signals corresponding to six different phase components can also be obtained by the configuration of the charge collecting electrodes illustrated in FIG. 11. However, by adopting the configuration illustrated in FIG. 12, the widths of the linear electrodes can be made wider than in the case of the configuration of FIG. 11. The spatial resolution obtained by the configuration illustrated in FIG. 12 is lower than that obtained by the configuration illustrated in FIG. 11. However, it becomes easier to connect the linear electrodes.

Figure 13:
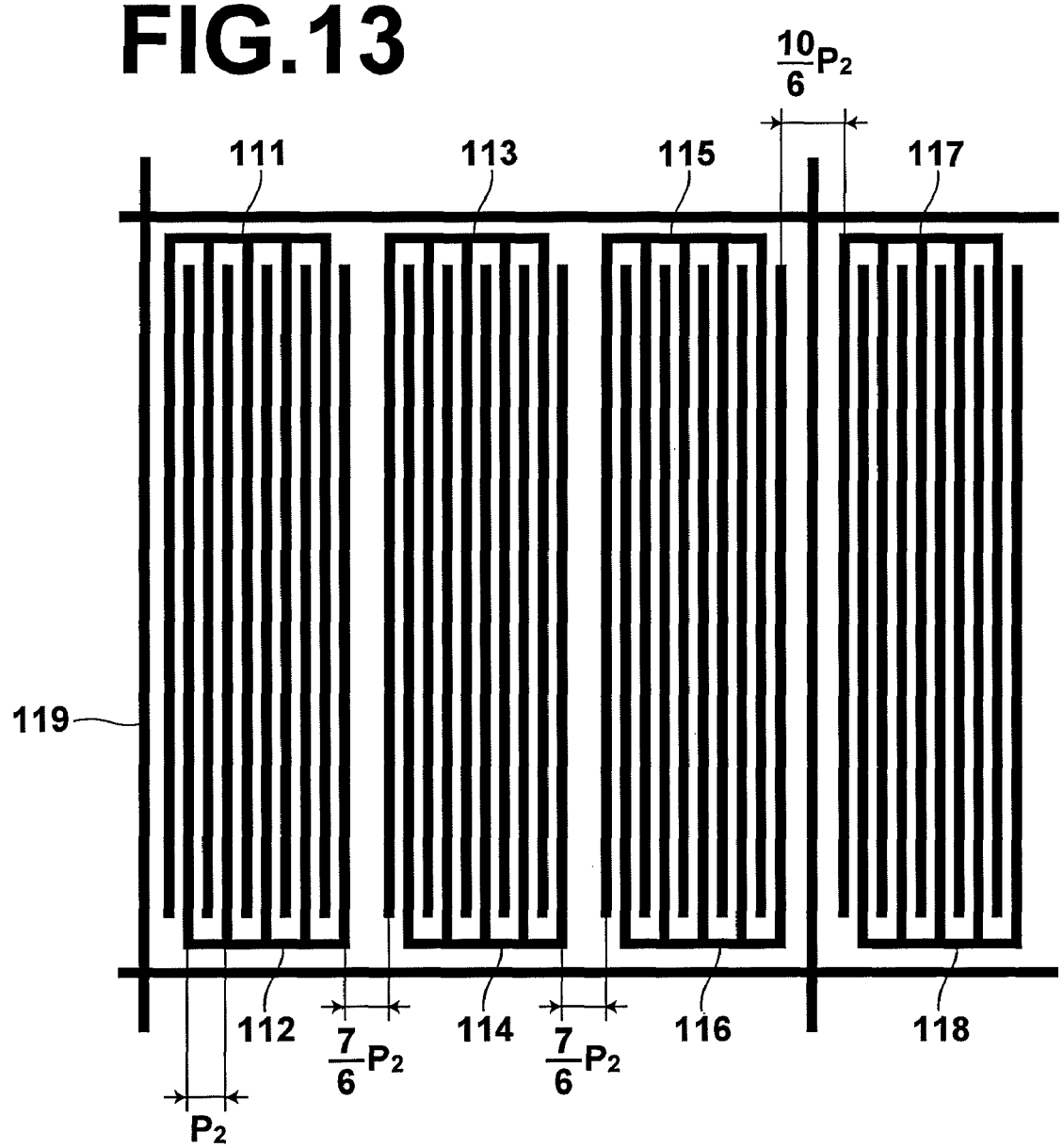
FIG. 13 is a diagram that illustrates a modification to the radiation image detector employed by the phase contrast radiation imaging apparatus of the first embodiment.

As illustrated in FIG. 13, constant potential linear electrodes 119 may be provided in a grid pattern to surround the first through sixth linear electrode groups 111 through 116 of each unit element 72. The advantageous effects provided by the constant potential linear electrodes 119 are the same as those described for the constant potential linear electrodes 90. Electric potentials are applied to the constant potential linear electrodes 119 such that electric potential differences among the surrounding charge collecting electrodes do not become great. That is, the electric potentials of the constant potential linear electrodes 119 are approximately the same as those of the charge collecting electrodes. More specifically, electric potentials equal to a grounded state or that approach a grounded state are applied. Note that in the case that the constant potential linear electrodes 119 are provided, the pitch between linear electrode groups of pixels adjacent in the direction perpendicular to the longitudinal directions of the linear electrodes, specifically, the pitch between the linear electrode group 116 and the linear electrode group 117, is set to (10/6)·$P_2$, as illustrated in FIG. 13.

Figure 14:
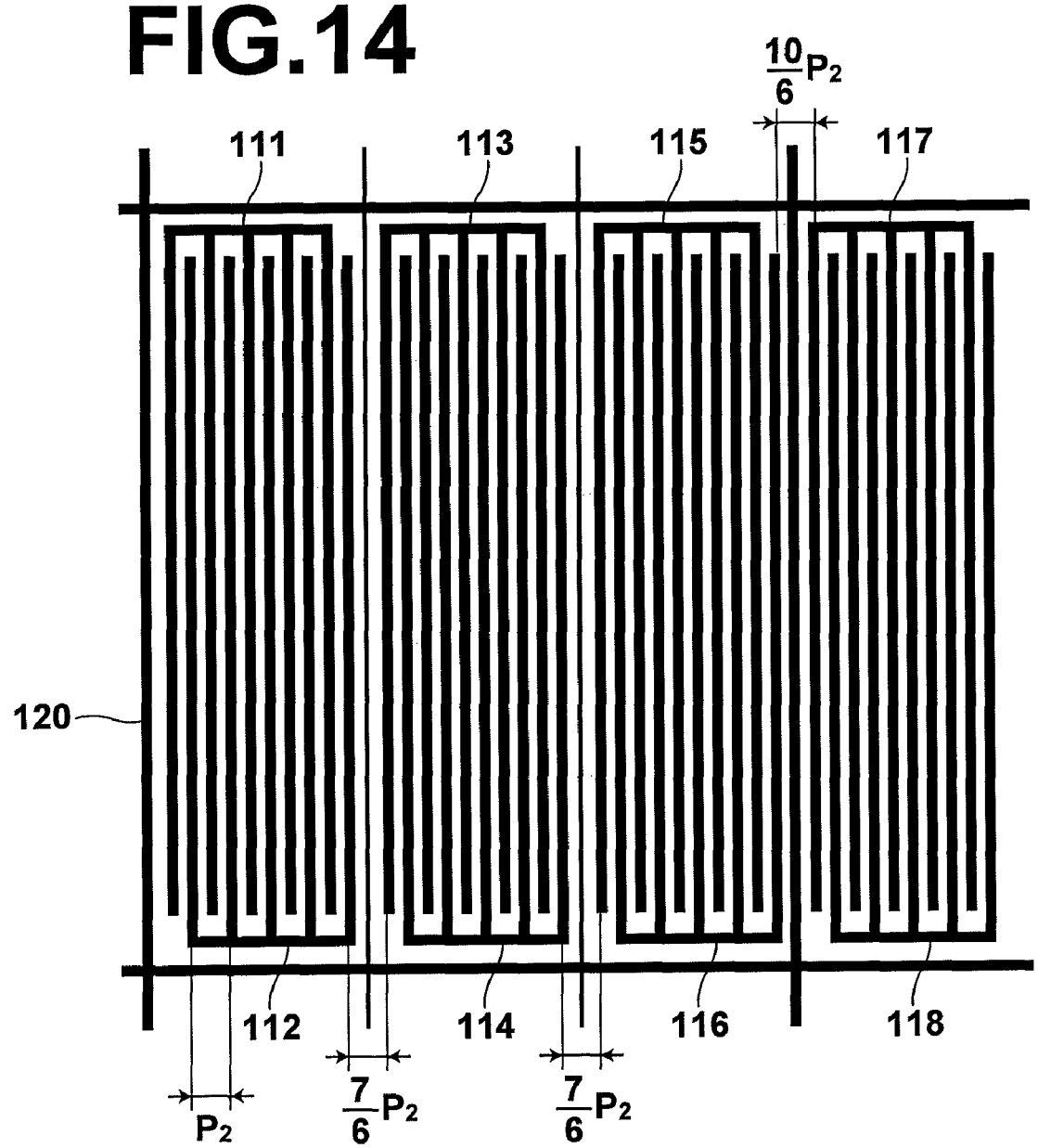
FIG. 14 is a diagram that illustrates a modification to the radiation image detector employed by the phase contrast radiation imaging apparatus of the first embodiment.

Alternatively, constant potential linear electrodes 120 may be provided to surround each sub pixel, as illustrated in FIG. 14.

Figure 15:
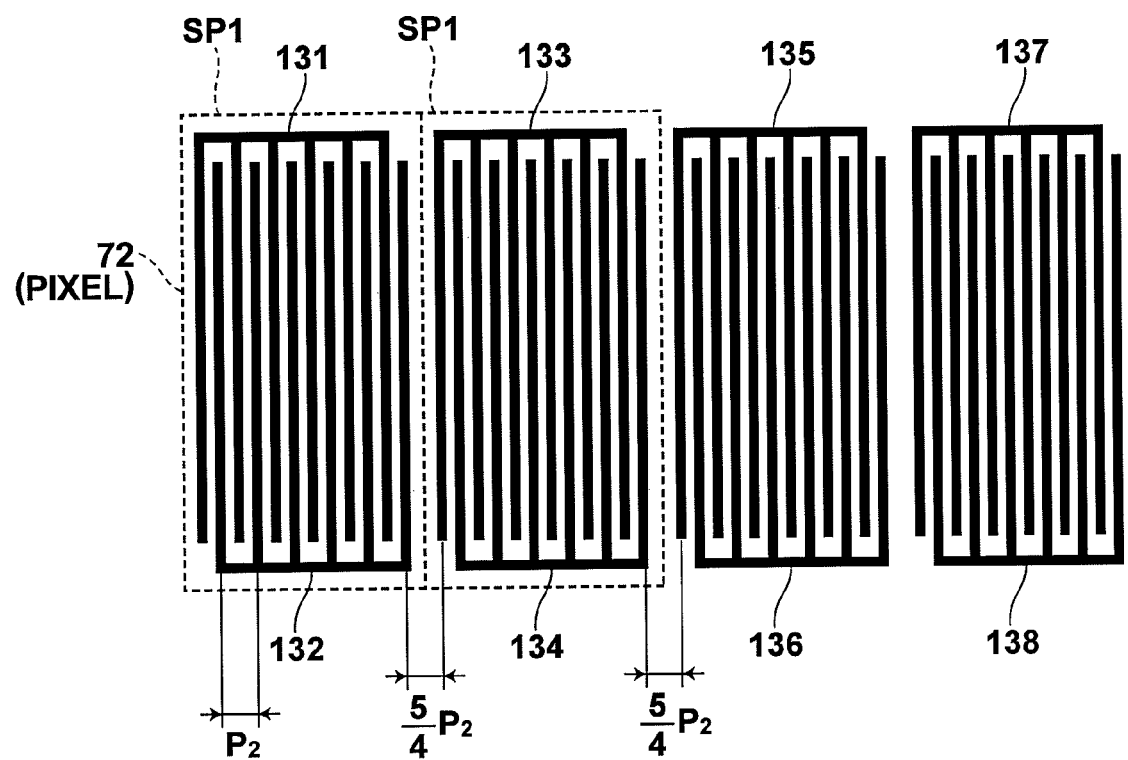
FIG. 15 is a diagram that illustrates a modification to the radiation image detector employed by the phase contrast radiation imaging apparatus of the first embodiment.

As a further alternative, a pixel corresponding to a single detection element 72 may be sectioned into two sub pixels, and linear electrode groups having different phases may be provided in each of the sub pixels, as illustrated in FIG. 15. In the modification illustrated in FIG. 15, a first linear electrode group 131 and a second linear electrode group 132, in which linear electrodes are arranged at a pitch $P_2$, are provided in a sub pixel SP1 with the phases in the arrangement periods thereof being shifted by π. A third linear electrode group 133 and a fourth linear electrode group 134, in which linear electrodes are arranged at a pitch $P_2$, are provided in a sub pixel SP2 with the phases in the arrangement periods thereof being shifted by π. Adjacent linear electrode groups of the sub pixel SP1 and the sub pixel SP2 are separated by a distance of 5$P_2$/4. Thereby, if the phase of the first linear electrode group 131 is designated as 0, the phase of the second linear electrode group 132 is π, the phase of the third linear electrode group 133 is 3π/2, and the phase of the fourth linear electrode group 134 is π/2. That is, the first through fourth linear electrode groups have phases which are different by π/2. Note that linear electrode groups 135 through 138 are linear electrode groups of an adjacent pixel. The linear electrode group 135 detects signals of the same phase as those detected by the first linear electrode group 131, the linear electrode group 136 detects signals of the same phase as those detected by the second linear electrode group 132, the linear electrode group 137 detects signals of the same phase as those detected by the third linear electrode group 133, and the linear electrode group 138 detects signals of the same phase as those detected by the fourth linear electrode group 134.

Image signals corresponding to four different phase components can be obtained with a single radiation imaging operation, by configuring the charge collecting electrodes as illustrated in FIG. 15. In this case, the electric charges collected by the first through fourth linear electrode groups 131 through 134 are read out for each linear electrode group.

In the modifications illustrated in FIG. 12 and FIG. 15, a pixel corresponding to a single detection element 72 is sectioned into three or two sub pixels. However, the present invention is not limited to these configurations, and pixels corresponding to single detection elements 72 may be sectioned into n (n≧4) sub pixels. In this case, if the pitch between linear electrode groups of adjacent sub pixels is set to (2n+1)$P_2$/2n, the linear electrode groups will have phases that differ by π/n.

If pixels corresponding to single detection elements 72 are sectioned into two or three sub pixels, data regarding four to six phase components can be obtained in a single imaging operation, and favorable phase images can be obtained. The configuration illustrated in FIG. 11 may be considered as an alternate configuration for obtaining data regarding four to six phase components with a single imaging operation. However, in the configuration illustrated in FIG. 11, the width of each linear electrode becomes narrow, and there is a possibility that problems will arise during manufacture thereof. Therefore, this configuration is not practical. Meanwhile, if the number n of sub pixels is greater than or equal to four while maintaining the pixel size, the number of linear electrodes in each linear electrode group decreases, and the resolution of data regarding phase components deteriorates.

In the case that the pixels are sectioned into pluralities of sub pixels as described above, it is desirable for the lengths of the linear electrodes of the pairs of linear electrode groups to be greater than the widths of the pairs of linear electrode groups in a direction perpendicular to the length directions thereof, as illustrated in FIGS. 12 through 15.

Figure 16:
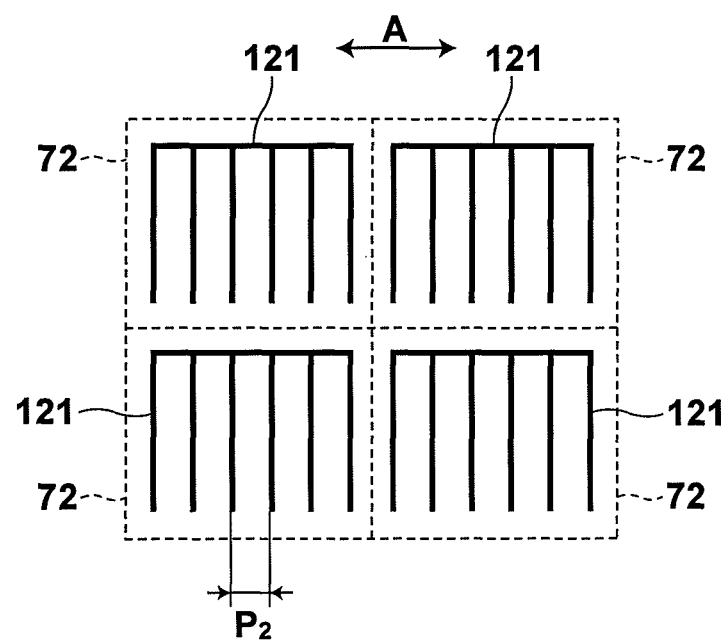
FIG. 16 is a diagram that illustrates a modification to the radiation image detector employed by the phase contrast radiation imaging apparatus of the first embodiment.

The modifications described above are cases in which pluralities of linear electrode groups are provided within each unit element 72. Alternatively, a single linear electrode group 121, in which linear electrodes are arranged at a pitch $P_2$, may be provided in each unit element 72, as illustrated in FIG. 16. Note that FIG. 16 illustrates the linear electrode groups 121 of four unit elements 72. Note that in the case that the charge collecting electrodes for each unit element 72 is constituted by a single linear electrode group as illustrated in FIG. 16 and image signals corresponding to different phase components are to be obtained, a moving mechanism may be provided. The moving mechanism moves the radiation image detector 40 and the diffraction grating 30 along the surfaces thereof in the direction perpendicular to the linear electrodes (the direction indicated by arrow A in FIG. 16). Radiation imaging may be performed a plurality of times accompanying the movement by the moving mechanism. For example, image signals corresponding to three phase components may be obtained by moving the radiation image detector 40 and the diffraction grating 30 for distances of ⅓ the pitch $P_2$, and performing radiation imaging at each position. Alternatively, image signals corresponding to six phase components may be obtained by moving the radiation image detector 40 and the diffraction grating 30 for distances of ⅙ the pitch $P_2$, and performing radiation imaging at each position.

Figure 17:
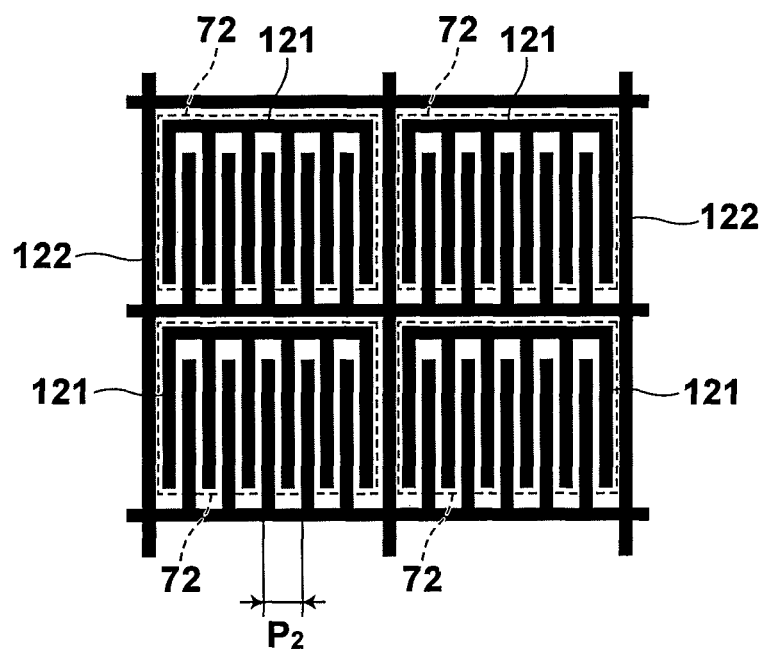
FIG. 17 is a diagram that illustrates a modification to the radiation image detector employed by the phase contrast radiation imaging apparatus of the first embodiment.

Constant potential linear electrodes 122 may be provided to the charge collecting electrodes in addition to the linear electrode groups 121, as illustrated in FIG. 17. The constant potential linear electrodes 122 are provided between each of the linear electrodes of the linear electrode groups 121 and as a grid surrounding each of the unit elements 72. The advantageous effects provided by the constant potential linear electrodes 122 are the same as those described for the constant potential linear electrodes 90. Electric potentials are applied to the constant potential linear electrodes 119 such that electric potential differences among the surrounding charge collecting electrodes do not become great. That is, the electric potentials of the constant potential linear electrodes 119 are approximately the same as those of the charge collecting electrodes. More specifically, electric potentials equal to a grounded state or that approach a grounded state are applied.

In the case that two linear electrode groups are provided in each unit element 72 as illustrated in FIG. 8, a moving mechanism that moves the radiation image detector 40 and the diffraction grating 30 along the surfaces thereof in the direction perpendicular to the linear electrodes may be provided. Radiation imaging may be performed a plurality of times accompanying the movement by the moving mechanism. For example, image signals corresponding to six phase components may be obtained by moving the radiation image detector 40 and the diffraction grating 30 for distances of ⅓ the pitch $P_2$, and performing radiation imaging at each position.

A case was described in which the first linear electrode group 81a and the second linear electrode group 81b are provided in each unit element 72 such that the phases thereof are shifted by π, with reference to FIG. 8. However, the present invention is not limited to such a configuration, and three linear electrode groups may be provided in each unit element 72 such that the phases thereof are shifted by 2π/3. By arranging the charge collecting electrodes in this manner, image signals corresponding to three phase components can be obtained with a single radiation imaging operation. That is, the number of radiation imaging operations can be reduced to a third of that in the case that a single linear electrode group is provided in each unit element 72. In addition, the charge collecting electrodes may be constituted by three linear electrode groups as described above, and a moving mechanism that moves the radiation image detector and the diffraction grating may be provided. In this case, image signals corresponding to six phase components may be obtained by moving the radiation image detector 40 and the diffraction grating 30 for distances of ½ the pitch $P_2$, and performing radiation imaging at each position.

Note that in the phase contrast radiation imaging apparatus of the first embodiment, a radiation image detector equipped with TFT switches was employed. However, the switching elements are not limited to being TFT switches, and CMOS's or CCD's may be utilized.

In addition, in the phase contrast radiation imaging apparatus of the first embodiment, a radiation image detector that records radiation images while positive voltage is applied to the upper electrode 50 has been described. However, the present invention is not limited to this configuration, and a radiation image detector of the TFT readout type that records radiation images while negative voltage is applied thereto may be employed.

Figure 18A:
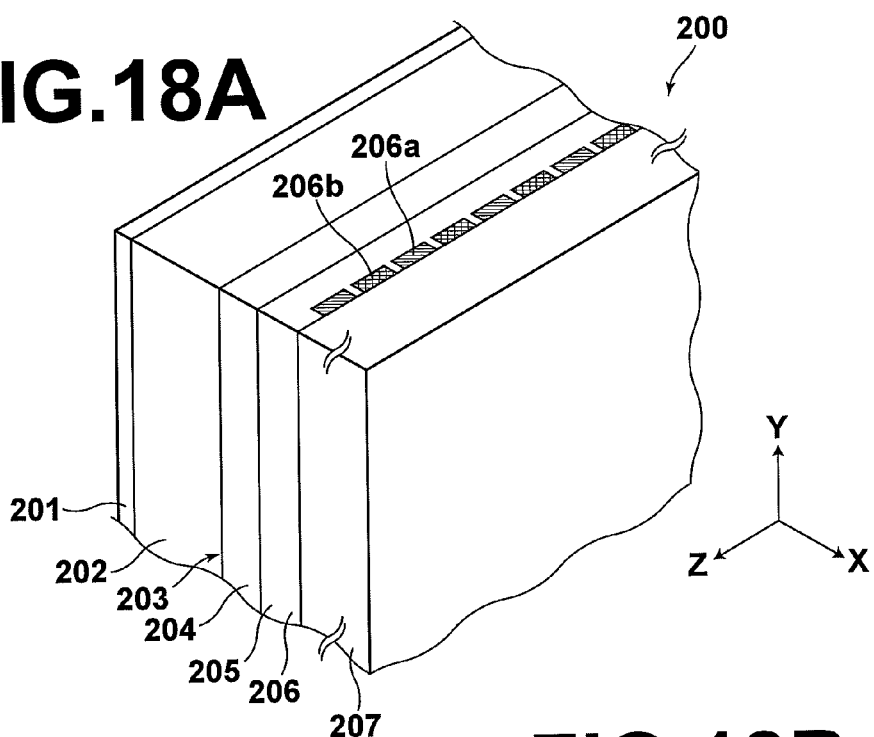
FIG. 18A is a sectional view that illustrates the schematic construction of a radiation image detector employed by a phase contrast radiation imaging apparatus according to a second embodiment of the present invention.
Figure 18B:
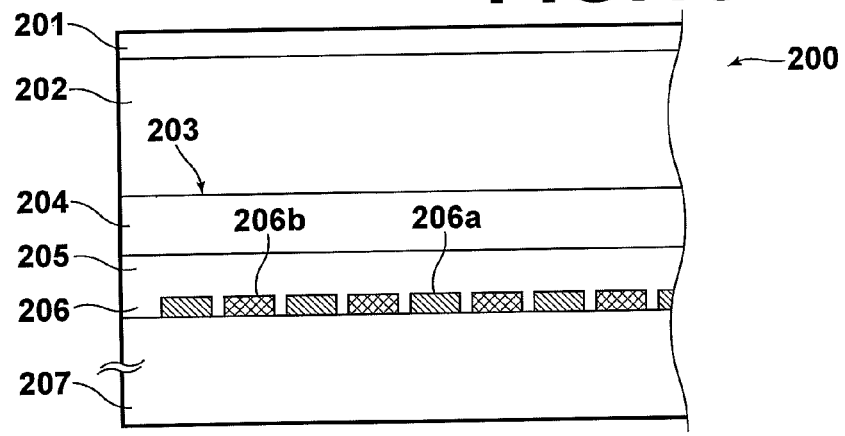
FIG. 18B is a sectional view of the radiation image detector of FIG. 18A, taken along an XZ plane.
Figure 18C:
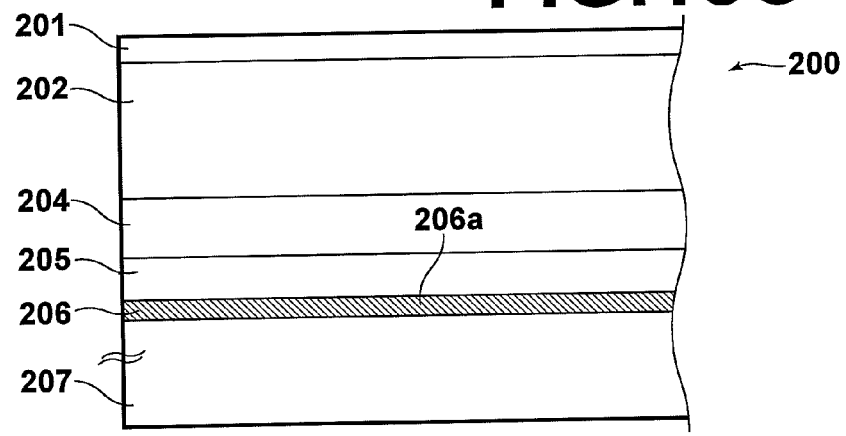
FIG. 18C is a sectional view of the radiation image detector of FIG. 18A, taken along an XY plane.

Next, a second embodiment of a phase contrast radiation imaging apparatus that employs a radiation image detector of the present invention will be described. The phase contrast radiation imaging apparatus of the second embodiment employs a radiation image detector of the optical readout type. The phase contrast radiation imaging apparatus of the second embodiment differs from the phase contrast radiation imaging apparatus of the first embodiment only in the structure of the radiation image detector 200. Therefore, the structure of the radiation image detector will be described hereinafter. FIG. 18A is a perspective view of the radiation image detector 200. FIG. 18B is a sectional view of the radiation image detector 200 taken along the XZ direction of FIG. 18A. FIG. 18C is a sectional view of the radiation image detector 200 taken along the XY direction of FIG. 18A.

As illustrated in FIGS. 18A, 18B, and 18C, the radiation image detector 200 of the phase contrast radiation imaging apparatus of the second embodiment is formed by: a first electrode layer 201 that transmits radiation; a recording photoconductive layer 202 that generates electric charges when irradiated by radiation which has passed through the first electrode layer 201; a charge transport layer 204 that functions as an insulator with respect to electric charges of one of the polarities from between the charge pairs generated within the recording photoconductive layer 202, and functions as a conductor with respect electric charges of the other polarity; a readout photoconductive layer 205 that generates electric charges when irradiated by readout light; and a second electrode layer 206, which are laminated in this order. A charge accumulating section 203, at which electric charges which are generated within the recording photoconductive layer 202 are accumulated, is formed at the vicinity of the interface between the recording photoconductive layer 202 and the charge transport layer 204. Note that the radiation image detector 200 is formed on a glass substrate 207, starting with the second electrode layer 206.

The first electrode layer 201 is formed by a material that transmits radiation. The first electrode layer 201 may be formed by NESA ($SnO_2$), ITO (Indium Tin Oxide), IDIXO (Idemitsu Indium X-metal Oxide by Idemitsu), which is an amorphous light transmissive oxide film, or the like, formed to a thickness of 50 nm to 200 nm. Alternatively, the first electrode layer 201 may be formed by Al or Au films or the like having a thickness of 100 nm.

The second electrode layer 206 includes a plurality of transparent linear electrodes 206a that transmit readout light, and a plurality of light blocking linear electrodes 206b. The transparent linear electrodes 206a and the light blocking linear electrodes 206b extend from one end of an image forming region of the radiation image detector 200 to the other end. As illustrated in FIGS. 18A and 18B, the transparent linear electrodes 206a and the light blocking linear electrodes 206b are alternately provided parallel to each other, with predetermined intervals therebetween.

The transparent linear electrodes 206 are formed by a conductive material that transmits readout light. ITO, IZO, or IDIXO at a thickness from 100 nm to 200 nm may be employed as the transparent linear electrodes 206, similar to the first electrode layer 201.

The light blocking linear electrodes 206b are formed by a conductive material that does not transmit readout light. However, it is desirable for the light blocking linear electrodes 206b to transmit erasing light. Therefore, combinations of the aforementioned conductive transparent materials and a color filter may be employed. The thickness of the light blocking linear electrodes 206b is within a range from 100 nm to 200 nm.

As will be described later, image signals are read out from pairs of adjacent transparent linear electrodes 206a and light blocking linear electrodes 206b. In the radiation image detector 200 of the second embodiment, 20 pairs of transparent linear electrodes 206a and light blocking linear electrodes 206b are provided within a width that corresponds to a single pixel unit, as illustrated in FIG. 19. That is, a first pair of linear electrodes 211, a second pair of linear electrodes 212, a third pair of linear electrodes 213, a fourth pair of linear electrodes 214, . . . a twentieth pair of linear electrodes are provided within the width corresponding to a single pixel unit. In the second embodiment, the term "pixel unit" refers only to sections in the direction perpendicular to the longitudinal direction of the linear electrodes. As illustrated in FIG. 19, the linear electrodes are arranged such that the interval between the first linear electrode pair 211 and the third linear electrode pair, and the interval between the second linear electrode pair 212 and the fourth linear electrode pair 214, that is, the intervals between every other pair of linear electrodes, is the pitch $P_2$. The pitch $P_2$ is set to be within a range from 2 μm to 15 μm. First linear electrode groups are constituted by $2n-1^{th}$ (n is an integer from 1 to 10) linear electrode pairs, and second linear electrode groups are constituted by $2n^{th}$ linear electrode pairs. The first and second linear electrode groups are alternatively and repeatedly arranged within the width corresponding to a single pixel unit in the direction perpendicular to the longitudinal direction of the linear electrodes. In this case, the phase in the arrangement periods of the first linear electrode groups and the second linear electrode groups are shifted by π. Note that although not illustrated in the drawings, the transparent linear electrodes 206a of the first linear electrode group are physically connected to each other by conductive wires. Likewise, the transparent linear electrodes 206a of the second linear electrode group are physically connected to each other by conductive wires.

The recording photoconductive layer 202 generates charge pairs when irradiated with radiation. The recording photoconductive layer 202 is formed by a film having a-Se as its main component and a thickness of approximately 500 μm. The film having a-Se as its main component is selected because a-Se is superior in that it has high quantum efficiency with respect to radiation, and high dark resistance. The thickness of the recording photoconductive layer 202 is within a range from 10 μm to 1500 μm. In the case that the radiation imaging is mammography, it is preferable for the thickness of the recording photoconductive layer 202 to be within a range from 150 μm to 250 μm. In the case that the radiation imaging is general radiation imaging, it is preferable for the thickness of the recording photoconductive layer 202 to be within a range from 500 μm to 1200 μm.

The charge transport layer 204 is formed by a material that exhibits a great difference ($10^2$ or greater, preferably $10^3$ or greater) in the mobility of electric charges which are charged in the first electrode layer 201 and the mobility of electric charges having the opposite polarity. Examples of such a material include: organic compounds, such as poly N vinyl carbazole (PVK), N,N'-diphenyl-N,N'-bis(3-methylphenyl)-[1,1'-biphenyl]-4,4'-diamine (TPD), and discotic liquid crystals; TPD polymer (polycarbonate, polystyrene, PVK) dispersoids; and semiconductor materials, such as a-Se doped with 10 to 200 ppm of C1. The thickness of the charge transport layer is within a range from 0.2 μm to 2 μm.

The readout photoconductive layer 205 generates charge pairs when irradiated by readout light L1 or erasing light L2. The readout photoconductive layer 205 is formed by a film of photoconductive material having a thickness of 5 μm to 20 μm, with at least one of: a-Se; Se—Te; Se—As—Te; metal-free phthalocyanine; metal phthalocyanine; MgPc (magnesium phthalocyanine); VoPc (phase II of vanadyl phthalocyanine); and CuPc (copper phthalocyanine) as its main component.

Next, the operation by which the phase contrast radiation imaging apparatus of the second embodiment records a radiation image onto the radiation image detector, and the operation by which the radiation image is read out, will be described.

The steps of the operation of the phase contrast radiation imaging apparatus of the second embodiment from emission of the radiation from the radiation irradiating section 10 through the formation of the self image of the diffraction grating 30 are the same as those in the phase contrast radiation imaging apparatus of the first embodiment, and therefore, descriptions thereof will be omitted.

Figure 20A:
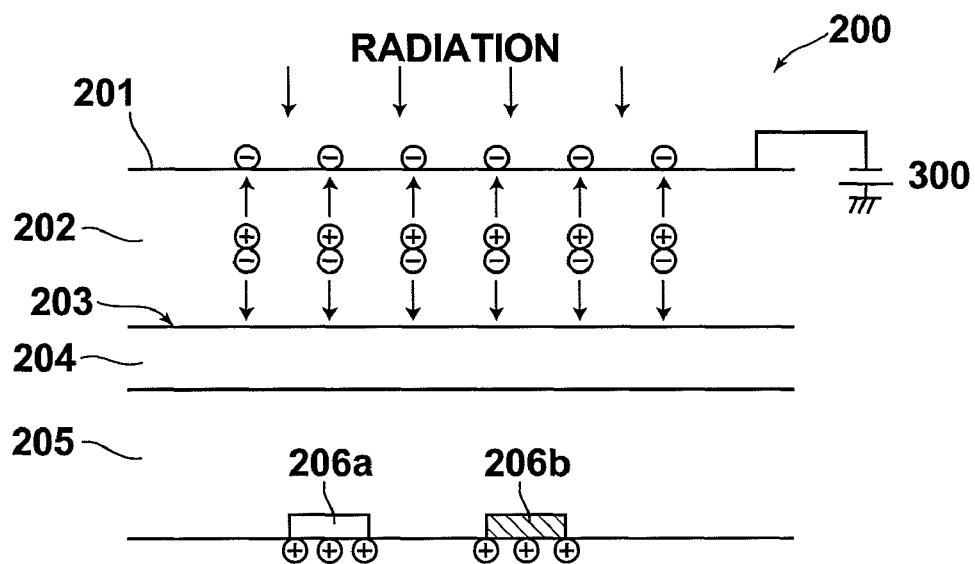
FIGS. 20A and 20B are diagrams for explaining a recording operation onto the radiation image detector employed by the phase contrast radiation imaging apparatus of the second embodiment of the present invention.

As illustrated in FIG. 20A, radiation that bears the self image formed by the Talbot effect of the diffraction grating 30 is irradiated onto the radiation image detector 40 from the side of the first electrode layer 201, in a state in which a high voltage source 300 is applying negative voltage to the first electrode layer 201.

Figure 20B:
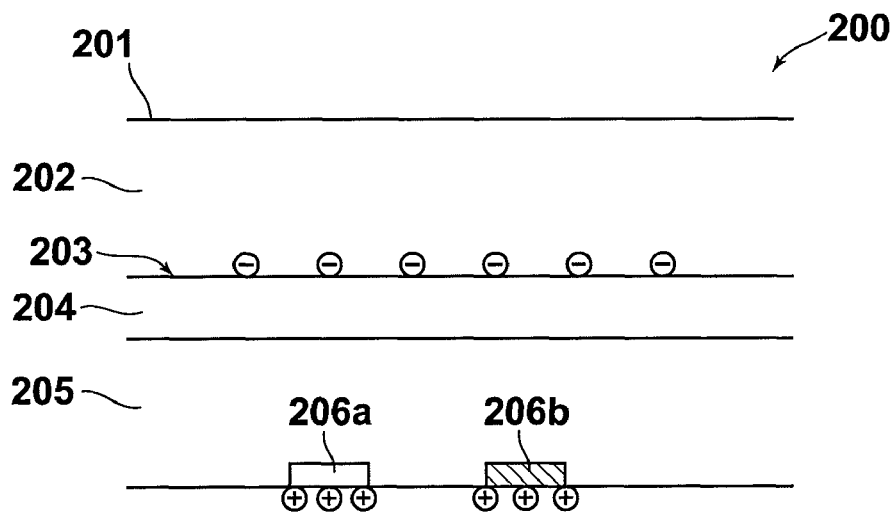

The radiation which is irradiated onto the radiation image detector 200 passes through the first electrode layer 201 and enters the recording photoconductive layer 202. The radiation causes charge pairs to be generated within the recording photoconductive layer 202. Positive electric charges from among the charge pairs combine with the positive charges charged on the first electrode layer 201 and disappear. On the other hand, negative electric charges from among the charge pairs are accumulated as latent image charges in the charge accumulating section 203 at the interface between the recording photoconductive layer 202 and the charge transfer layer 204 (refer to FIG. 20B).

In the radiation image detector 200 of the phase contrast radiation imaging apparatus, the second electrode layer 206 for collecting the electric charges at the charge accumulating section 203 are constituted by the transparent linear electrodes 206a and the light blocking linear electrodes 206b. Accordingly, when the voltage is applied to the first electrode layer 201 as described above, electric fields which are parallel to the linear electrodes of second electrode layer 206, that is, perpendicular to the surface of the first electrode layer 201, are formed within the recording photoconductive layer 202. The negative charges which are generated within the recording photoconductive layer 202 travel along the electric fields without being dispersed, and are collected at the charge accumulating section 203. Therefore, the transparent linear electrodes 206a and the light blocking linear electrodes 206b perform substantially equivalent functions as a combination of an amplitude diffraction grating and a detector. Accordingly, electric charges that represent image contrast generated by a combination of the deformed self image of the diffraction grating 30 and the practical diffraction grating formed by the first linear electrode groups are accumulated at the charge accumulating section 203 at positions above the first electrode groups (constituted by the 2n–1$^{th}$ pairs of linear electrodes). Likewise, electric charges that represent image contrast generated by a combination of the deformed self image of the diffraction grating 30 and the practical diffraction grating formed by the second linear electrode groups are accumulated at the charge accumulating section 203 at positions above the first electrode groups (constituted by the 2n–1$^{th}$ pairs of linear electrodes). The image contrast is generally represented as Moire fringes. As described above, the phases of the first linear electrode groups and the second linear electrode groups are shifted by π. Therefore, signals that correspond to two types of phase components, of which the phases are shifted by π, are detected by the radiation image detector 200.

Figure 21:
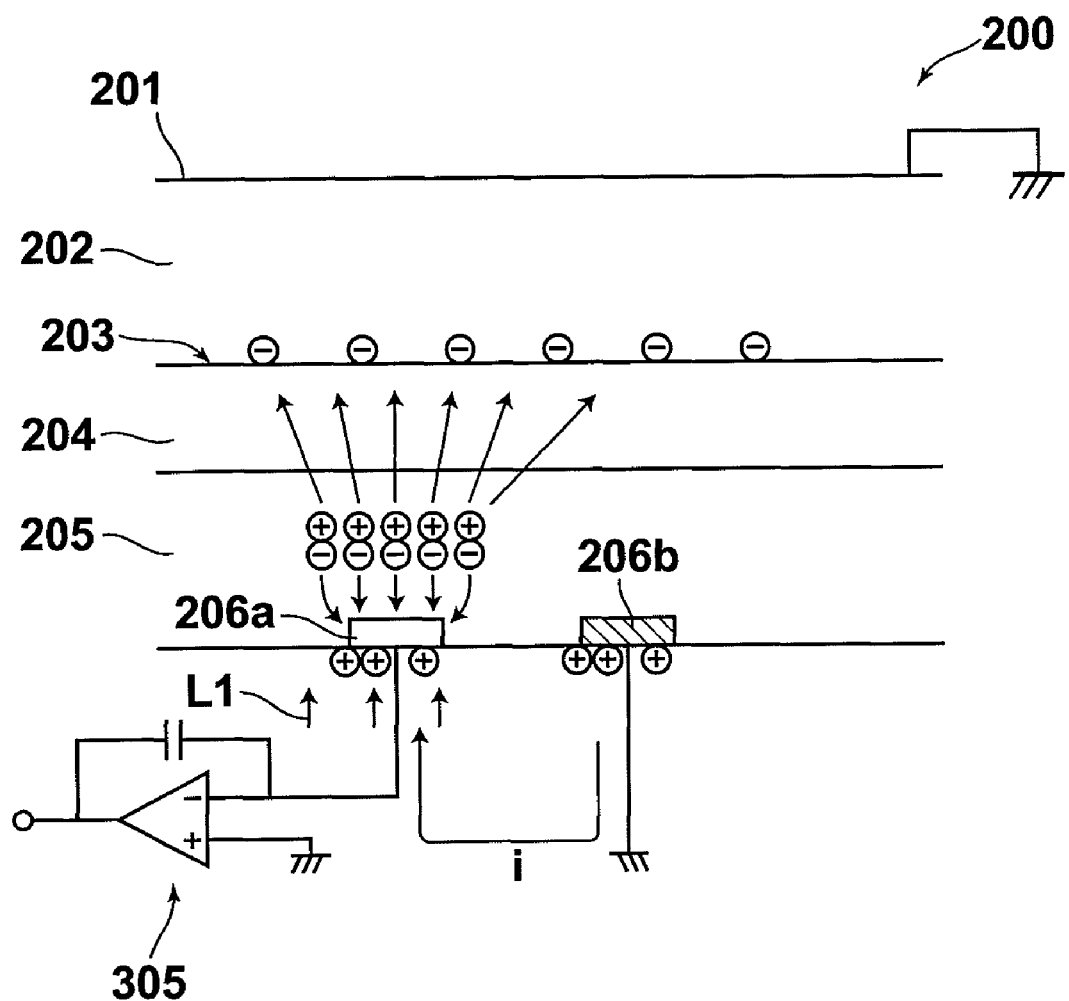
FIG. 21 is a diagram for explaining a readout operation from the radiation image detector employed by the phase contrast radiation imaging apparatus of the second embodiment of the present invention.

Next, the first electrode layer 201 is grounded, and readout light L1 is irradiated from the side of the second electrode layer 206, as illustrated in FIG. 21. The readout light L1 is transmitted through the transparent linear electrodes 206a, and enters the readout photoconductive layer 205. Charge pairs are generated within the readout photoconductive layer 205 due to irradiation of the readout light L1. Positive electric charges from among the charge pairs combine with the latent image charges, which are accumulated at the charge accumulating section 203. At the same time, negative electric charges from among the charge pairs combine with the positive charges of the charged second electrode layer 206, via charge amplifiers 305.

The combinations of the negative charges, which are generated in the readout photoconductive layer 205, and the positive charges, which are charged in the light blocking linear electrodes 206b, cause current to flow through the charge amplifiers 305. The current is integrated and detected as image signals.

At this time, the electric charges that flow from the first linear electrode group constituted by the first linear electrode pair 211 and the third linear electrode pair 213 illustrated in FIG. 19 are detected as image signals corresponding to a first phase component. Meanwhile, the electric charges that flow from the second linear electrode group constituted by the second linear electrode pair 212 and the fourth linear electrode pair 214 illustrated in FIG. 19 are detected as image signals corresponding to a second phase component.

The subject 20 and the inner structures thereof can be detected, by analyzing the image signals corresponding to the first phase components and the image signals corresponding to the second phase components which are detected by the radiation image detector 200.

Note that in the phase contrast radiation imaging apparatus of the second embodiment, a moving mechanism that moves the radiation image detector 200 and the diffraction grating 30 along the surfaces thereof in the direction perpendicular to the linear electrodes may be provided. Radiation imaging may be performed a plurality of times accompanying the movement by the moving mechanism. For example, image signals corresponding to six phase components may be obtained by moving the radiation image detector 40 and the diffraction grating 30 for distances of ⅓ the pitch $P_2$, and performing radiation imaging at each position.

In addition, similarly to the first embodiment, pairs of linear electrode groups, in which linear electrode groups are arranged in order, may be arranged at different positions such that the phases thereof are different. In this case, image signals corresponding to a number of phase components sufficient to form a phase image can be obtained without the aforementioned moving mechanism.

In the phase contrast radiation imaging apparatus of the second embodiment, a radiation image detector that records radiation images while negative voltage is applied to the first electrode layer 201 has been described. However, the present invention is not limited to this configuration, and a radiation image detector of the optical readout type that records radiation images while positive voltage is applied thereto may be employed.

When image signals corresponding to a plurality of phase components are obtained by the phase contrast radiation imaging apparatuses of the first and second embodiments, the image signals can be employed to calculate phase shift differential images (an angular distribution image that illustrates how radiation is bent by the refraction effect of a subject) and phase shift images (in which phase shift differentials are integrated). These images may be utilized according to the purpose of imaging. Regarding calculation methods for phase shift differential images and phase shift images, refer to U.S. Pat. No. 7,180,979, for example.

In the phase contrast radiation imaging apparatuses of the first and second embodiments, the subject or the phase contrast radiation imaging apparatus (the radiation irradiating section 10, the diffraction grating 30 and the radiation image detector 40 or 200) may be rotated or moved to obtain images from a plurality of imaging directions. Then, calculation processes may be administered onto the plurality of images, to observe the subject and the inner structures thereof three dimensionally. In this case, the three dimensional image is formed from refractive index distributions, and visualization of structures which are difficult to visualize with conventional tomography or tomosynthesis becomes possible.

In the phase contrast radiation imaging apparatuses of the first and second embodiments, three dimensional images may be constructed from the obtained signals that correspond to the plurality of phase components. Desired tomographic images may be generated from the three dimensional images as well.

Figure 22:
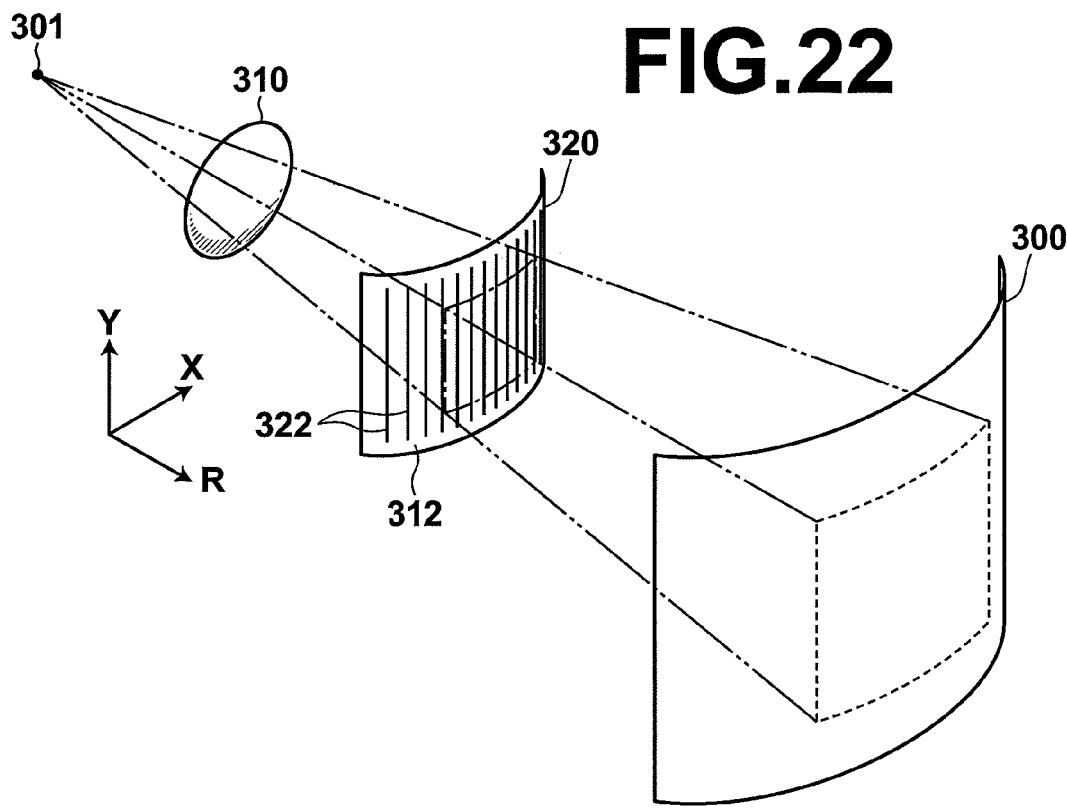
FIG. 22 is a diagram that schematically illustrates the construction of a phase contrast radiation imaging apparatus according to a third embodiment of the present invention.
Figure 23:
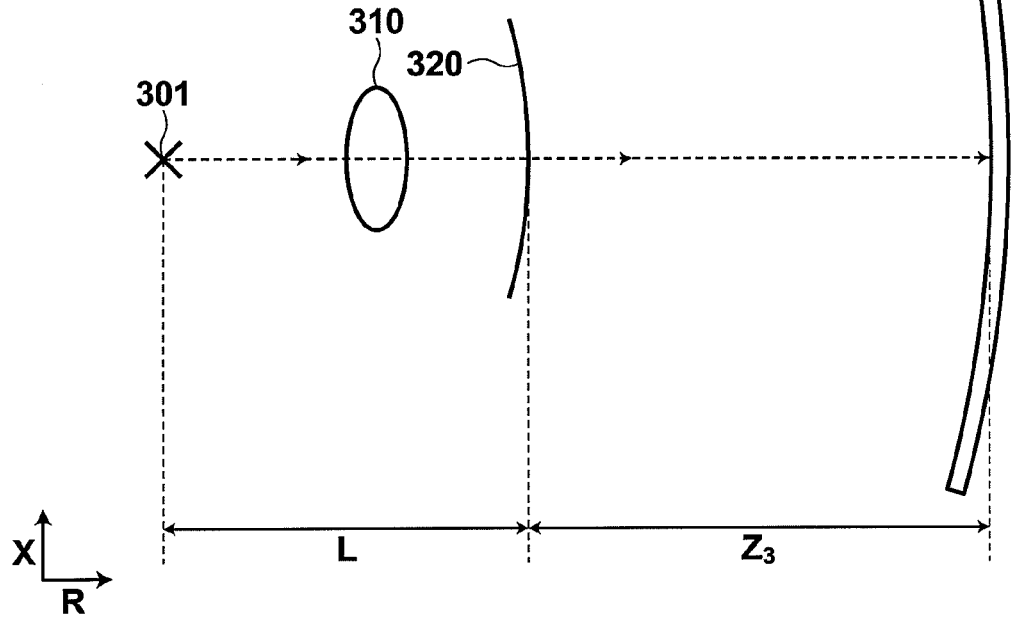
FIG. 23 is a plan view of the phase contrast radiation imaging apparatus of FIG. 22.

Next, a phase contrast radiation imaging apparatus according to a third embodiment of the present invention will be described. FIG. 22 is a diagram that illustrates the schematic construction of the phase contrast radiation imaging apparatus of the third embodiment. FIG. 23 is a plan view of the phase contrast radiation imaging apparatus of FIG. 22. Note that the direction perpendicular to the drawing sheet of FIG. 23 corresponds to the Y direction in FIG. 22.

As illustrated in FIG. 22, the phase contrast radiation imaging apparatus of the third embodiment is equipped with: a radiation source 301 that emits radiation toward a subject 10; a diffraction grating 320, onto which the radiation emitted from the radiation source 301 is irradiated, and which is configured to generate the Talbot effect when irradiated by the radiation; and a radiation image detector 300 that detects the radiation, which is diffracted by the diffraction grating 320.

The radiation source 301 has spatial interference properties that cause the Talbot effect to occur when it emits radiation onto the diffraction grating 320. For example, if the size of the light emitting spot (that is, the diameter of the aperture of the radiation source) is approximately 30 microns, the spatial interference properties approximately five meters away or greater from the radiation source are those that cause the Talbot effect. A micro focus X ray tube or a plasma X ray source may be utilized as the radiation source 301. If a standard radiation source, which is comparatively large in size, is employed, a multi slit that the radiation is caused to pass through may be provided at the radiation emitting side of the radiation source. The details of such a structure are described in F. Pfeiffer et al., "Phase retrieval and differential phase-contrast imaging with low-brilliance X-ray sources", Nature Physics Letters, Vol. 2, No. 1, pp. 258-261, 2006. It is necessary for the pitch $P_0$ of the multi slit to satisfy the following equation:

$$P_0 = P_2 \times L / Z_3$$

Note that $P_2$ is the pitch of linear electrodes (distances along an arcuate surface) of the radiation image detector 300, L is the distance from the radiation source 301 (in the case that a multi slit is employed, the position of the multi slit) to the diffraction grating 320, and $Z_3$ is the distance from the diffraction grating 320 to the radiation image detector 300.

Figure 24:
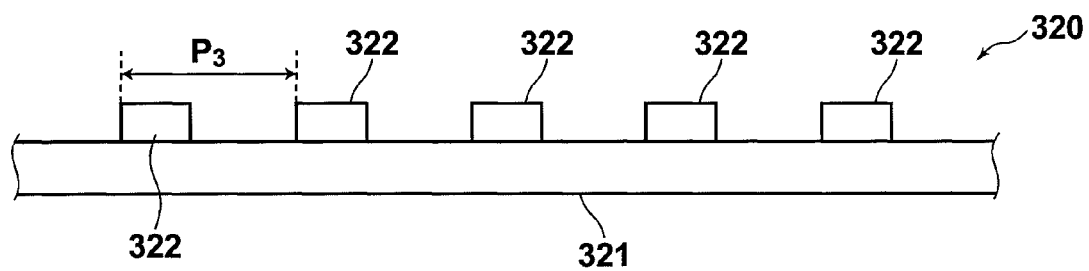
FIG. 24 is a schematic diagram that illustrates the construction of a diffraction grating.

As illustrated in FIG. 24, the diffraction grating 320 is equipped with a substrate 321 and a plurality of diffraction members 322 which are attached to the substrate 321. All of the plurality of diffraction members 322 are linear, and extend unidirectionally (the direction perpendicular to the drawing sheet of FIG. 24). The pitch $P_3$ at which the diffraction members 322 are provided (that is, the period of the diffraction grating) is constant in the third embodiment (assuming a case in which the diffraction members are attached to the curved arcuate surface). Gold, for example, may be employed as the material of the diffraction members 322 of the diffraction grating 320. It is preferable for the diffraction members 322 to be those that constitute a so called phase diffraction grating, by which phase modulation of approximately 80° to 100° (more preferably 90°) is imparted onto the radiation irradiated thereon. In the X ray energy band employed for general medical diagnostics, the necessary thickness of the gold is within a range from 1 µm to several µm.

To facilitate understanding, the diffraction grating 320 is represented as a plane in FIG. 24. however, in the phase contrast radiation imaging apparatus of the third embodiment, the diffraction grating 320 is curved in shape, as illustrated in FIG. 23. Specifically, the diffraction grating 320 is formed as an arcuate surface which has a line that passes through the radiation source 301 and extends in the longitudinal direction of the diffraction members 322 of the diffraction grating 320 as its central axis. A transparent flexible substrate may be employed, the diffraction members 322 may be formed on the flexible substrate, and then the flexible substrate may be adhesively attached to a base material which is of an arcuate shape, in order to produce the diffraction grating 320. Alternatively, a thin glass substrate which is reinforced by plastic film may be employed, the diffraction members 322 may be formed on the reinforced glass substrate, then the reinforced glass substrate may be adhesively attached to a base material which is of an arcuate shape, in order to produce the diffraction grating 320.

Detectors similar to those which have been described as the first and second embodiments and the modifications thereof may be utilized as the radiation image detector 300. In addition, however, the radiation image detector 300 which is utilized by the third embodiment is shaped as a curved surface, as illustrated in FIG. 23. Specifically, the radiation image detector 300 is formed as an arcuate surface which has a line that passes through the radiation source 301 and extends in the longitudinal direction of the diffraction members 322 of the diffraction grating 320 (a line that passes through the radiation source 301 and extends perpendicular to the drawing sheet of FIG. 23) as its central axis. A transparent flexible substrate may be employed as the substrate 71 of the active matrix 70, the unit elements 72 may be formed on the flexible substrate, then the flexible substrate may be adhesively attached to a base material which is of an arcuate shape. Thereafter, the semiconductor layer 60 and the upper electrode 50 may be formed on the active matrix substrate 71, in order to form the radiation image detector 300. Note that the unit elements 72 may be formed on the flexible substrate, the semiconductor layer 60 and the upper electrode 50 may be formed on the active matrix substrate 71, and then the active matrix substrate 71, the semiconductor layer 60, and the upper electrode 50 may be adhesively attached to a base material which is of an arcuate shape. If this method is adopted, however, the semiconductor layer 60 may crack or peel off, depending on the thickness thereof.

Alternatively, a thin glass substrate which is reinforced by plastic film may be employed as the substrate 71. Note that in the case that light is irradiated onto the radiation image detector 300 from the side of the substrate, it is desirable for a transparent substrate and a transparent base material to be employed.

Next, the conditions necessary for the diffraction grating 320 and the radiation image detector 300 to constitute a Talbot interferometer will be explained. First, a coherence length l is expressed by the following equation:

$$l = \frac{\lambda}{a/(L+Z_3)}$$

wherein:

λ: the wavelength of radiation (generally the central wavelength)

a: the diameter of the aperture of the radiation source 301 in the direction substantially perpendicular to the longitudinal direction of the diffraction members 322

L: the distance from the radiation source 301 (in the case that a multi slit is employed, the position of the multi slit) to the diffraction grating 320 (refer to FIG. 23)

$Z_3$: the distance from the diffraction grating 320 to the radiation image detector 300

In addition, it is necessary for the distance $Z_3$ from the diffraction grating 320 to the radiation image detector 300 to satisfy the following equation, in the case that the diffraction grating 320 is a phase diffraction grating:

$$Z_3 = \left(m + \frac{1}{2}\right)\frac{P_3^2}{\lambda}$$

wherein:

m: 0 or a positive integer

λ: the wavelength of radiation

Note that the conditions for the distance $Z_3$ in the case that the diffraction grating 320 is an amplitude diffraction grating are expressed by the following equation:

$$Z_3 = \left(m + \frac{1}{2}\right)\frac{P_3^2}{\lambda}$$

wherein:

m: 0 or a positive integer

λ: the wavelength of radiation

The operation of the phase contrast radiation imaging apparatus of the third embodiment is the same as that of the phase contrast radiation imaging apparatuses of the first and second embodiments.

Note that in the phase contrast radiation imaging apparatus of the third embodiment as well, a moving mechanism that moves the radiation image detector 300 and the diffraction grating 320 along the surfaces thereof in the direction perpendicular to the linear electrodes may be provided. Radiation imaging may be performed a plurality of times accompanying the movement by the moving mechanism. For example, image signals corresponding to six phase components may be obtained by moving the radiation image detector 300 and the diffraction grating 320 for distances of ⅓ the pitch $P_2$, and performing radiation imaging at each position.

If a phase diffraction grating is employed as the diffraction grating 320 in the phase contrast radiation imaging apparatus of the third embodiment, the thickness of the diffraction grating 320 is thin. Therefore, radiation is not blocked by the diffraction members 322, even if the radiation enters the diffraction grating 320 at an angle. Accordingly, it is not necessary to form the diffraction grating 320 as an arcuate surface, and the diffraction grating 320 may be formed as a planar surface. However, in the case that the diffraction grating 320 is formed as a planar surface, it is desirable for the intervals between the diffraction members 322 to become wider at positions remote from the center of the diffraction grating 320.

Here, a method for calculating pitches $P_{(x)}$, at which the diffraction members 322 are provided, at locations (r, x) which are distances x away from a position Q, at which the central axis C of a radiation beam intersects with the diffraction grating 320.

Figure 25:
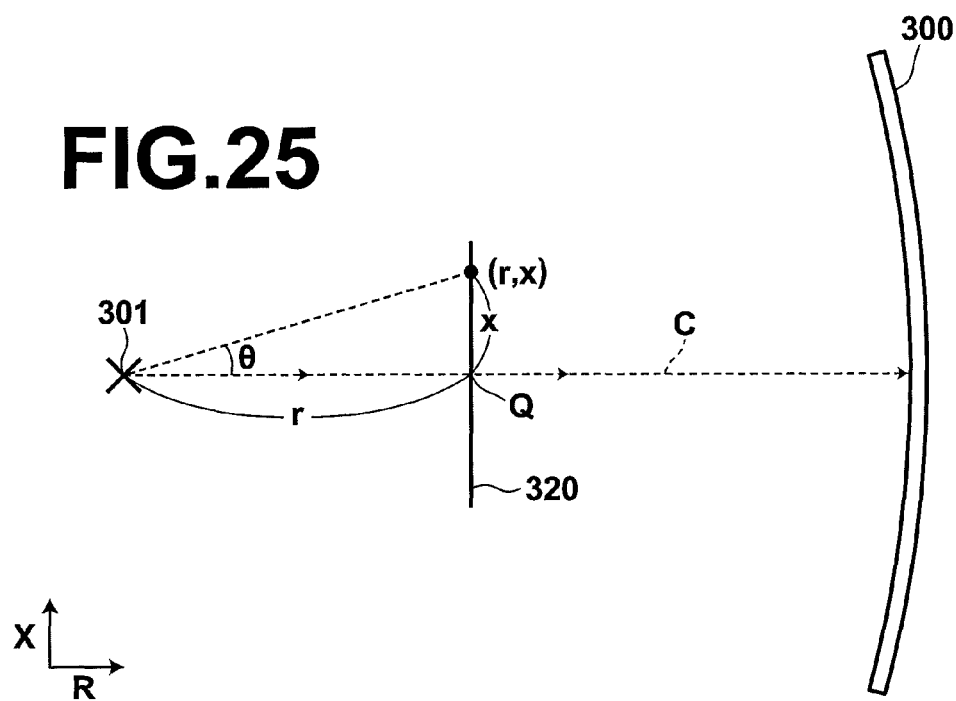
FIG. 25 is a diagram for explaining variations in the pitch at which diffraction members are provided in the diffraction grating in the phase contrast radiation imaging apparatus of the third embodiment of the present invention.

The pitch $P_{(x)}$ can be represented by the following formula (refer to FIG. 25. FIG. 25 is a plan view of the of the phase contrast radiation imaging apparatus of FIG. 22. Note that the direction perpendicular to the drawing sheet of FIG. 25 corresponds to the Y direction in FIG. 22).

$$P_{(x)} = r\Delta\theta \times \frac{\tan\theta}{\theta} \times \left\{\sqrt{(r^2 + x^2)} \times \frac{1}{r}\right\} \times \frac{1}{\cos\theta}$$

wherein:

r: the distance from the radiation source 301 (in the case that a multi slit is employed, the position of the multi slit) to the diffraction grating 320

$r\Delta\theta$: the pitch at the position Q, at which the central axis C of a radiation beam intersects with the diffraction grating 320

Because $x/r=\tan\theta$, if this is substituted into the above formula, $P_{(x)}$ can be represented by the following equation:

$$P_{(x)} = r\Delta\theta \times \frac{\tan\theta}{\theta} \times \frac{\sqrt{1 + \tan^2\theta}}{\cos\theta} = r\Delta\theta \times \frac{\tan\theta}{\theta\cos^2\theta}$$

The shape of the diffraction grating 320 is not limited to the arcuate surface or the planar surface described above. The diffraction grating 320 may be of any shape, as long as the projected image thereof onto an arcuate surface is grating fringes having equidistance intervals therebetween. Specific examples of these alternate shapes include: elliptic arcuate surfaces; parabolic surfaces; and hyperbolic surfaces. Among these shapes, the planar surface is the simplest to manufacture and is therefore desirable. However, in the case that the diffraction grating 320 is moved, slight errors will occur unless the diffraction grating 320 is of the arcuate shape.

The radiation image detector 300 is formed into an arcuate shape in the phase contrast radiation imaging apparatus of the third embodiment. Therefore, radiation images which are reproduced from image data based on period data obtained by the radiation image detector 300 represent the subject faithfully. However, physicians who perform diagnosis based on radiation images may be more familiar with radiation images which are obtained by conventional radiation imaging apparatuses that utilize flat image detectors. Accordingly, there may be cases in which diagnosis is difficult.

Figure 26:
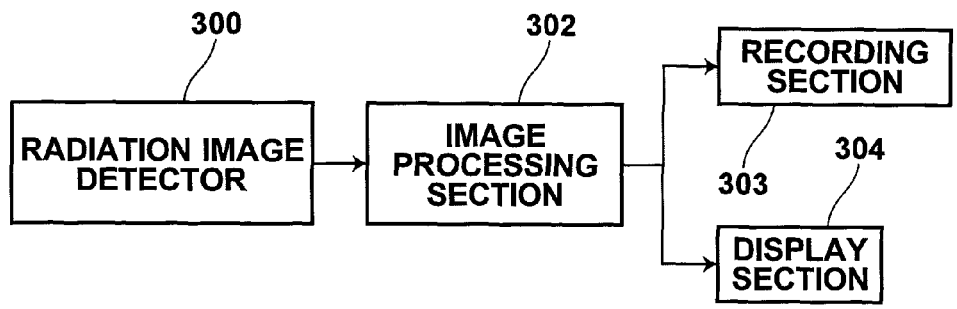
FIG. 26 is a diagram for explaining an image processing section of the phase contrast radiation imaging apparatus of the third embodiment of the present invention.

Therefore, an image processing section 302 may be provided as illustrated in FIG. 26. The image processing section 302 may administer image processes onto image data, which are obtained based on phase component data detected by the radiation image detector 300, such that the image data represents a radiation image formed by radiation which has been diffracted by the diffraction grating 320 and projected onto a planar surface. Specifically, an image process may be administered that magnifies radiation imaged at locations remote from the centers thereof. The processed image data may be recorded into predetermined recording media by a recording section 303 or displayed as radiation images by a display section 304, to provide physicians with radiation images which are easy to diagnose.

Figure 27:
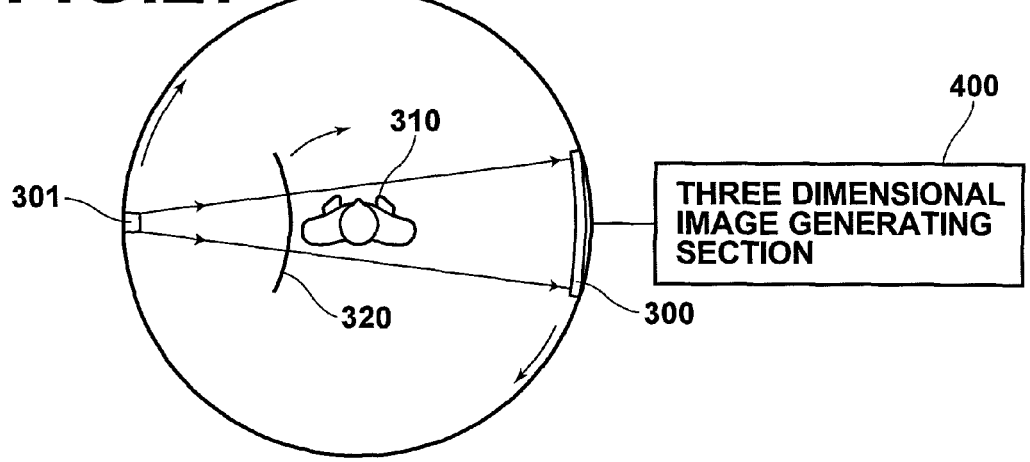
FIG. 27 is a diagram that illustrates a phase X ray CT apparatus, to which the phase contrast radiation imaging apparatus of the third embodiment of the present invention has been applied.

The phase contrast radiation imaging apparatus of the third embodiment may be applied to a phase contrast X ray CT apparatus. Specifically, a rotating mechanism that rotates the radiation source 301, the diffraction grating 320 and the radiation image detector 300 integrally about a subject 310 who is placed between the radiation source 301 and the radiation image detector 300 may be provided, as illustrated in FIG. 27. Three dimensional images of the subject 310 may be generated based on a plurality of image data sets detected by the radiation image detector 300 accompanying the movement by the rotating mechanism, by a three dimensional image generating section 400.

Note that in the case that the phase contrast radiation imaging apparatus of the third embodiment is applied to the phase contrast X ray CT apparatus, it is desirable for the radiation image detector to be configured to be able to obtain all necessary phase data within a single imaging operation.

Figure 28:
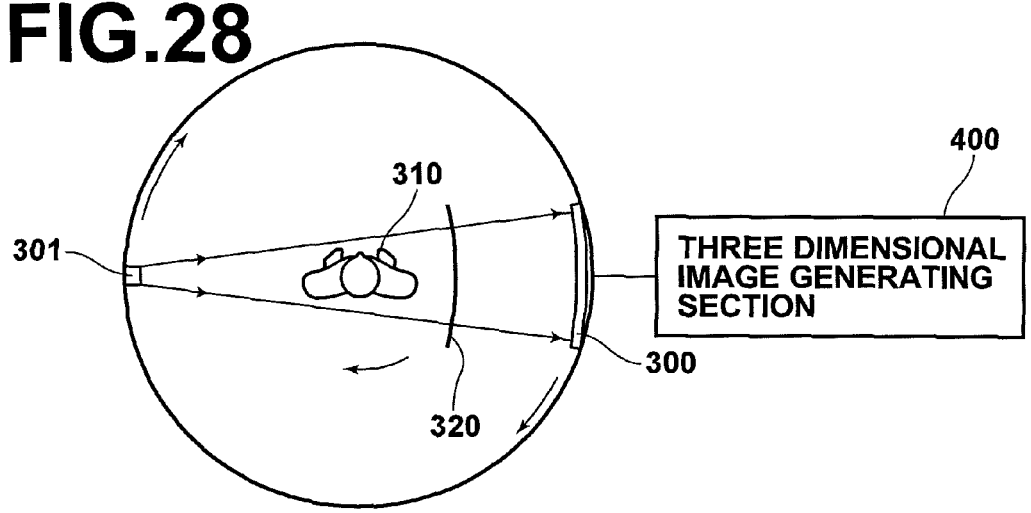
FIG. 28 is a diagram that illustrates a phase X ray CT apparatus, to which the phase contrast radiation imaging apparatus of the third embodiment of the present invention has been applied.

The placement of the subject 310 may be between the diffraction grating 320 and the radiation image detector 300 as illustrated in FIG. 27. Alternatively, the subject 310 may be placed between the radiation source 301 and the diffraction grating 320. Note that FIG. 27 and FIG. 28 merely illustrate positional relationships among the radiation source 301, the diffraction grating 320, the radiation image detector 300 and the subject 310. That is, FIG. 27 and FIG. 28 do not accurately represent the distance between the radiation source 301 and the diffraction grating 320, or the distance between the diffraction grating 320 and the radiation image detector 300. The distance between the radiation source 301 and the diffraction grating 320 and the distance between the diffraction grating 320 and the radiation image detector 300 are set such that conditions for generating the Talbot effect described above are satisfied.

The method by which three dimensional images are generated based on the plurality of image data sets of the subject 310 detected by the radiation image detector 300 are the same as those for conventional X ray CT apparatuses.

What is claimed is:

1. A radiation image detector, comprising:
   a charge generating layer that generates electric charges when radiation bearing a radiation image is irradiated thereon; and
   charge collecting electrodes that collect the electric charges which are generated in the charge generating layer;
   the charge collecting electrodes being constituted by a plurality of linear electrode groups, which are electrically independent from each other;

the linear electrode groups being constituted by a plurality of linear electrodes, which are arranged at a constant period and electrically connected to each other; and the plurality of linear electrode groups being provided such that the phases thereof are different.

2. A radiation image detector as defined in claim 1, wherein:

the plurality of linear electrode groups are arranged to form at least two pairs of linear electrode groups, which are arranged alternately such that the phase of the arrangement period thereof are opposite each other.

3. A radiation image detector as defined in claim 2, wherein:

the lengths of the linear electrodes of the pairs of linear electrode groups are greater than the widths of the pairs of linear electrode groups in a direction perpendicular to the length directions thereof.

4. A radiation image detector as defined in claim 2, further comprising:

constant potential linear electrodes, which are provided to surround each of the pairs of linear electrode groups and have substantially the same electrical potential as the charge collecting electrodes.

5. A radiation image detector as defined in claim 2, further comprising:

constant potential linear electrodes, which are provided to surround the pairs of the plurality of linear electrode groups that correspond to each of the pixel units that constitute the radiation image and have substantially the same electrical potential as the pairs of the plurality of linear electrode groups.

6. A phase contrast radiation imaging apparatus, comprising:

a radiation source;

a diffraction grating, into which radiation emitted from the radiation source enters; and a radiation image detector defined in claim 1, onto which the radiation which has passed through the diffraction grating is irradiated;

the diffraction grating being configured such that Talbot's effect is generated when radiation is irradiated thereon; and the radiation image detector detecting signals that correspond to phase components.

7. A phase contrast radiation imaging apparatus as defined in claim 6, wherein:

at least the radiation image detector, from among the diffraction grating and the radiation image detector, is formed along an arcuate surface, which has a line that passes through the radiation source and extends in the longitudinal direction of diffraction members of the diffraction grating as its central axis.

8. A phase contrast radiation imaging apparatus as defined in claim 7, wherein:

the diffraction grating is a phase diffraction grating; and the diffraction grating projects an image of grating fringes having equidistant intervals therebetween onto the arcuate surface.

9. A phase contrast radiation imaging apparatus as defined in claim 7, wherein:

the diffraction grating is formed along an arcuate surface, which has a line that passes through the radiation source and extends in the longitudinal direction of the diffraction member of the diffraction grating as its central axis.

10. A phase contrast radiation imaging apparatus as defined in claim 6, wherein:

phase components, which are necessary to form a phase image, are obtained without moving the diffraction grating and the radiation image detector relative to each other when detecting the signals that correspond to the phase components.

11. A phase contrast radiation imaging apparatus as defined in claim 7, further comprising:

a radiation image output section that administers image processes onto image data, which are obtained based on period data detected by the radiation image detector, such that the image data represents a radiation image formed by radiation which has been diffracted by the diffraction grating and projected onto a planar surface, and outputs the processed image data.

12. A phase contrast radiation imaging apparatus as defined in claim 6, further comprising:

a moving mechanism that moves the radiation source, the diffraction grating and the radiation image detector integrally with respect to a subject which is placed between the radiation source and the radiation image detector; and an image constructing section that constructs desired tomographic images or a three dimensional image of the subject, based on a plurality of sets of image data which are detected by the radiation image detector during movement thereof by the moving mechanism.

* * * * *